United States Patent [19]
Woo et al.

[11] Patent Number: 6,066,624
[45] Date of Patent: *May 23, 2000

[54] GENE THERAPY FOR SOLID TUMORS USING ADENOVIRAL VECTORS COMPRISING SUICIDE GENES AND CYTOKINE GENES

[75] Inventors: Savio L. C. Woo; Shu-Hsia Chen, both of Houston, Tex.

[73] Assignee: Baylor College of Medicine, Houston, Tex.

[*] Notice: This patent is subject to a terminal disclaimer.

[21] Appl. No.: 08/600,942

[22] PCT Filed: Aug. 25, 1994

[86] PCT No.: PCT/US94/09784

§ 371 Date: Feb. 15, 1996

§ 102(e) Date: Feb. 15, 1996

[87] PCT Pub. No.: WO95/05835

PCT Pub. Date: Mar. 2, 1995

Related U.S. Application Data

[63] Continuation-in-part of application No. 08/112,745, Aug. 26, 1993, Pat. No. 5,631,236.

[51] Int. Cl.$^7$ ..................................................... A61K 48/00
[52] U.S. Cl. ............................................ 514/44; 424/93.2
[58] Field of Search ............................... 514/44; 424/93.2

[56] References Cited

U.S. PATENT DOCUMENTS 5,529,774  6/1996  Barba et al. .

OTHER PUBLICATIONS

Blau et al (Nov. 2, 1995) New Eng. J. Med. 1204–1207.
Crystal (1995) Science 270, 404–410.
Miller et al (1995) FASEB J. 9, 190–199.
Verma et al (1997) Nature 389, 239–242.
Russell (1994) Eu. J. Cancer 30A, 1165–1171.
Ross et al (1996) Human Gene Therapy 7, 1781–1790.
Blaese et al (994) Eu. J. Cancer 30A 1190–1193/.
Denning et al (1997) Human Gene Therapy 8, 1825–1835.
Ledley (1995) Human Gene Therapy 6, 1129–144.
Mullen (1994) Pharm. Ther. 63, 199–207.
Gansbacher et al (1993) Cancer Invest. 11, 345–354.
Huber et al (1993) Cancer Res. 53, 4619–4626.
Gansbacher et al. (1990) J. Exp. Med. 172, 1217–1224.
Boviatsis, E. et al., Long–term Survival of Rats Harboring Brain Neoplasms Treated with Ganciclovir and a Herpes Simplex Virus Vector that Retains an Intact Thymidine Kinase Gene, Cancer Research 54:5745–5751 (1994).
Boviatsis, E. et al., Gene transfer into Experimental Brain Tumors Mediated by Adenovirus, Herpes Simplex Virus, and Retrovirus Vectors, Human Gene Therapy 5:183–191 (1994).
Zhang, J.–F. et al., Treatment of a Human Breast Cancer Xenograft with an Adenovirus Vector Containing an Interferon gene Results in Rapid Regression Due to Viral Oncolysis and Gene Therapy, Proc. Natl. Acad. Sci. USA 93:4513–4518 (1996).
Hallahan, D. et al., Spatial and Temporal Control of Gene Therapy Using Ionizing Radiation, Nature Medicine 1:786–791 (1995).
O'Malley, B. et al., Adenovirus–mediated Gene Therapy for Human Head and Neck Squamous Cell Cancer in a Nude Mouse Model, Cancer Research 55:1080–1085 (1995).
Leimig, T. et al., High–Efficiency Transduction of Freshly Isolated Human Tumor Cells Using Adenoviral Interleukin–2 Vectors, Human Gene Therapy 7:1233–1239 (1996).
Vieweg et al (1995) Cancer Invest. 13, 193–201.
Huber et al (1993) Cancer Res 53, 4619–4626.
"Report and Recommendations of the Panel to Acess the NIH Investment in Research on Gene Therapy", Orkin et al, 1995.
Karlsson, S., et al.; Stable gene transfer and tissue–specific expression of a human globin gene using adenoviral vectors; The EMBO J.; 5:2377–85 (1986).
Rosenfeld, M. A.; et al.; In Vivo Transfer of Human Cystic Fibrosis Transmembrane Conductance Regulator Gene to the Airway Epithelium; Cell; 68:143–55 (1992).
Quantin, B., et al; Adenovirus as an expression vector in muscle cells in vivo; Proc. Natl. Acad. Sci. USA; 89:2581–84 (1992).
Lemarchand, P., et al.; Adenovirus–mediated transfer of a recombinant human $\alpha_1$–antitrypsin cDNA to human endothelial cells; Proc. Natl. Acad. Sci. USA; 89;6482–86 (1992).
Jaffe, H. A., et al.; Adenovirus–mediated in vivo gene transfer and expression in normal rat liver; nature *genetics*; 1:372–78 (1992).
Stratford–Perricaudet, L. D., et al; Widespread Long–term Gene Transfer to Mouse Skeletal Muscles and Heart; J. Clin. Invest.; 90:626–30 (1992).

(List continued on next page.)

*Primary Examiner*—Deborah Crouch
*Attorney, Agent, or Firm*—Fulbright & Jaworski, L.L.P.

[57] ABSTRACT

The present invention provides a novel method of treating localized solid tumors and papillomas in an individual, as well as metastatic carcinomas. The method comprises delivering a suicide gene, by way of a recombinant adenoviral vector or other DNA transport system, into the tumor, papilloma or wart of an individual. Subsequently, a prodrug, such as the drug gaciclovir™, is administered to the individual. Additionally, the present invention provides a method for treating solid tumors, papillomas, warts and metastatic carcinomas, said method comprising introducing both a suicide gene and one or more cytokine genes into the tumor, papilloma or wart of an individual, and subsequently administering a prodrug to the individual. The methods of the present invention may be used to treat several different types of cancers and papillomas, including colon carcinoma, prostate cancer, breast cancer, lung cancer, melanoma, hepatoma, brain lymphoma and head and neck cancer.

45 Claims, 27 Drawing Sheets

OTHER PUBLICATIONS

Gomez–Foix, A. M., et al; Adenovirus–mediated Transfer of the Muscle Glycogen Phosphorylase Gene into Hepatocytes Confers Altered Regulation of Glycogen Metabolism; J. Bio. Chem.; 267:25129–34 (1992).

Mastrangeli, A., et al.; Diversity of Airway Epithelial Cell Targets for In Vivo Recombinant Adenovirus–mediated Gene Transfer; J. Clin. Invest.; 91:225–34 (1993).

Le Gal La Salle, G., et al.; An Adenovirus Vector for Gene Transfer into Neurons and Glia in the Brain; Science; 259:988–90 (1993).

Davidson, B. L., et al.; A model system for in vivo gene transfer into the central nervous system using an adenoviral vector; nature *genetics*; 3:219–23 1993).

Bajocchi, G., et al.; Direct in vivo gene transfer to ependymal cells in the central nervous system using recombinant adenovirus vectors; nature *genetics*; 3:229–34 (1993).

Haddada, H., et al.; Efficient Adenovirus–Mediated Gene Transfer Into Human Blood Monocyte–Derived Macrophages; Biochem. and Biophy. Res. Comm.; 195:1174–83 (1993).

Perricaudet, M., et al.; Use of Adenovirus For Cytokine–Encoding Gene Transfer In Vivo; J. of Oncology; 3:135 (1992).

Haddada; H., et al.; Adenoviral Interleukin–2 Gene Transfer into P815 Tumor Cells Abrogates Tumorigenicity and Induces Antitumoral Immunity in Mice; Hum. Gene Ther.; 4:703–11 (1993).

Smythe, W. R.; Use of Recombinant Adenovirus to Transfer the Herpes Simplex Virus Thymidine Kinase (HSVtk) Gene to Thoracic Neoplasms: An Effective in Vitro Drug Sensitization System; Cancer Res.; 54:2205–59 (1994).

Brody, S. L.; Direct In Vivo Gene Transfer and Expression in Malignant Cells Using Adenovirus Vectors; Hum. Gene Ther.; 5:437–47 (1994).

Gray, et al.; Antisense DNA Inhibition of Tumor Growth Induced by c–Ha–*ras* Oncogene in Nude Mice; Cancer Res. 53:577–80 (1993).

Fujiwara, et al.; Induction of Chemosensitivity in Human Lung Cancer Cells in Vivo by Adenovirus–mediated Transfer of the Wild–Type p53 Gene; Cancer Res. 54:2287–91 (1994).

Ezzeddine, et al.; Selective Killing of Glioma Cells in Culture and in Vivo by Retrovirus Transfer of the Herpes Simplex Virus Thymidine Kinase Gene; The New Biologist 6:608–14 (1991).

Hann, et al.; Antitumor Effect of Deferoxamine on Human Hepatocellular Carcinoma Growing Athymic Nude Mice; Cancer 8:2051–56 (1992).

Pantazis, et al.; Camptothecin Derivatives Induce Regression of Human Ovarian Carcinomas Grown in Nude Mice and Distinguish Between Non–Tumorigenic and Tumorigenic Cells In Vitro; Int. J. Cancer 53:863–71 (1993).

Wakeling, et al.; A Potent Specific Pure Antiestrogen with Clinical Potential; Cancer Res. 51:3867–73 (1991).

Pietras, et al.; Antibody to HER–2/*neu* receptor blocks DNA repair after cisplatin in human breast and ovarian cancer cells; Oncogene 9:1829–38 (1994).

Ogura; Implantation of Genetically Manipulated Fibroblasts into Mice as Antitumor α–Interferon Therapy; Cancer Res. 50:5102–06 (1990).

Gastl, et al.; Retroviral Vector–mediated Lymphokine Gene Transfer into Human Renal Cancer Cells; Cancer Res. 52:6229–36 (1992).

Stratford–Perricaudet, et al.; Evaluation of the Transfer and Expression in Mice of an Enzyme–Encoding Gene Using a Human Adenovirus Vector; Human Gene Therapy; 1:241–256 (1990).

O'Malley, et al.; Adenovirus–mediated Gene Therapy for Human Head and Neck Squamous Cell Cancer in a Nude Mouse Model; Cancer Research; 55:1080–1085 (1995).

Chen, et al.; Combination gene therapy for liver metastasis of colon carcinoma in vivo; Proc. Natl. Acad. Sci. USA; 92:2577–2581 (1955).

Bonnekoh, et al.; Inhibition of Melanoma Growth by Adenoviral–Mediated HSV Thymidine Kinase Gene Transfer In Vivo; J. Invest. Dermatol.; 104:313–317 (1995).

Chen, et al.; Gene therapy for brain tumors: Regression of experimental gliomas by adenovirus–mediated gene transfer in vivo; Proc. Natl. Acad. Sci. USA; 91:3054–3057 (1994).

Smythe, et al.; Successful Adenovirus–Mediated Gene Transfer in an In Vivo Model of Human Malignant Mesothelioma; Ann. Thorac. Surg.; 57:1395–401 (1994).

Perez–Cruet, et al.; Adenovirus–Mediated Gene Therapy of Experimental Gliomas; J. Neurosci. Res.; 39:506–511 (1994).

Caruso; et al.; Regression of established macroscopic liver metastases after in situ transduction of a suicide gene; Proc. Natl. Acad. Sci. USA; 90:7024–7028 (1993).

Langdon, S. et al.; Types of Immunodeficiency in Mice (Chapter 2); The Nude Mouse in Oncology Research; edited by E. Boven and B. Winograd; CRC Press Inc. (1991).

Fodstad, O.; Transplantability of Human Tumors (Chapter 6;) The Nude Mouse in Oncology Research; edited by E. Boven and B. Winograd; CRC Press Inc. (1991).

Winograd, B.; New Drug Development (Chapter 22;) The Nude Mouse in Oncology Research; edited by E. Boven and B. Winograd; CRC Press Inc. (1991).

Hajdu, S. I., et al.; The Nude Mouse as a Diagnostic Tool in Human Tumor Cell Research (Chapter 12); The Nude Mouse in Experimental and Clinical Research; vol. 2; edited by J. Fogh and B. C. Giovanella; Academic Press Inc. (1982).

Giovanella, B., et al.; Present and Future Trends in Investigation with the Nude Mouse as a Recipient of Human Tumor Transplants (Chapter 14); The Nude Mouse in Experimental and Clinical Research; vol. 2; edited by J. Fogh and B. C. Giovanella; Academic Press Inc. (1982).

Balser, G. A., et al.; Brain Tumor Research with Nude Mice (Chapter 22); The Nude Mouse in Experimental and Clinical Research; vol. 2; edited by J. Fogh and B. C. Giovanella; Academic Press Inc. (1982).

Xu, X. et al., Adenovirus–Mediated Interferon— Transfer Inhibits Growth of Transplanted HTLV–1 Tax Tumors in Mice, Human Gene Therapy 7:471–477 (1996).

Abe et al., In Vivo Antitumor Effect of Cytotoxic T Lymphocytes Engineered to Produce Interferon— by Adenovirus–Mediated Genetic Transduction, Biochem. and Biophys. Res. Comm. 218:164–170(1996).

Bramson, J. et al., Construction of a Double Recombinant Adenovirus Vector Expressing a Heterodimeric Cytokine: In Vitro and In Vivo Production of a Biologically active Interleukin–12, Human Gene therapy 7:333–342 (1996).

Trinh, Q. et al., Enzyme/prodrug Gene Therapy: Combination of Cytosine Deaminase/5–Fluorocytosine Versus thymidine kinase/Ganciclovir Enzyme/Prodrug Systems in a Human Colorectal Carcinoma Cell Line, Cancer Research 55:4808–4812 (1995).

Sugaya, S. et al., Inhibition of Tumor Growth by Direct Intratumoral Gene transfer of Herpes Simplex Virus Thymidine Kinase Gene with DNA–Liposome Complexes, Human Gene Therapy 7:223–230 (1996).

Oellig, C. and Seliger, B., Gene Transfer Into Brain Tumor Cell Lines: Reporter Gene Expression Using Various Cellular and Viral Promoters, J. of Neuroscience Res. 26:390–396 (1990).

Cheng, L. et al., In Vivo Promoter Activity and Transgene Expression in Mammalian Somatic Tissues Evaluated by Using Particle Bombardment, Proc. Natl. Acad. Sci. USA 90:4455–4459 (1993).

Martin–Gallardo, A. et al., A Comparison of Bovine Growth–Hormone Gene Expression in Mouse L Cells Directed by the Moloney Murine–Leukemia Virus Long Terminal Repeat, Simian Virus–40 Early Promoter or Cytomegalovirus Immediate Early–Promoter, Gene 70: 51–56 (1988).

Pasleau, F. et al., Growth Hormone Gene Expression in Eukaryotic Cells Directed by the Rous Sarcoma Virus Long Terminal Repeat or Cytomegalovirus Immediate–Early Promoter, Gene 38:227–232 (1985).

Rettinger, S. et al., Liver–Directed Gene Therapy: Quantitative Evaluation of Promoter Elements by Using In Vivo Retroviral Transduction, Proc. Natl. Acad. Sci. USA 91:1460–1464 (1993).

Overbeek, P. et al., Tissue–Specific Expression in Transgenic Mice of a Fused Gene Containing RSV Terminal Sequences, Science 231:1574–1576 (1986).

Gorman, C. et al., The Rous Sarcoma Virus Long Terminal Repeat is a Strong Promoter When Introduced Into a Variety of Eukaryotic Cells by DNA–Mediated Transfection, Proc. Natl. Acad. Sci. USA 79:6777–6781 (1982).

Ido, A. et al., Gene Therapy for Hepatoma Cells Using a Retrovirus Vector Carrying Herpes Simplex Virus Thymidine Kinase Gene Under the Control of Human —Fetoprotein Gene Promoter, Cancer Research 55:3105–3109 (1995).

Su, H. et al., Selective Killing of AFP–Positive Hepatocellular Carcinoma Cells by Adeno–Associated Virus Transfer of the Herpes Simplex Virus Thymidine Kinase Gene, Human Gene Therapy 7:463–470 (1996).

Carroll, N. et al., Enhancement of Gene Therapy Specificity for Diffuse Colon Carcinoma Liver Metastases with Recombinant Herpes Simplex Virus, Annals of Surgery 224:323–330 (1996).

Mullen, C. et al., Treatment of Microscopic Pulmonary Metastases with Recombinant Autologous Tumor Vaccine Expressing interleukin 6 and *Escherichia coli* Cytosine Deaminase Suicide Genes, Cancer Research 56:1361–1366 (1996).

Hoganson, D. et al., Comparison of the Effects of Three Different Toxin Genes and Their Levels of Expression on Cell Growth and Bystander Effect in Lung Adenocarcinoma, Cancer Research 56:1315–1323 (1996).

Mroz, P. and Moolten, F., Retrovirally Transduced *Escherichia coli* gpt Genes Combine Selectability with Chemosensitivity Capable of Mediating Tumor Eradication, Human Gene Therapy 4:589–595 (1993).

Moolten, F., Drug Sensitivity ("suicide") Genes for Selective Cancer Chemotherapy, Cancer Gene Therapy 1:279–287 (1994).

Chen, L. et al., Sensitization of Human Breast Cancer Cells to Cyclophosphamide and Ifosfamide by Transfer of a Liver Cytochrome P450 Gene, Cancer Research 56:1331–1340 (1996).

O'Malley, B. et al., Combination Gene Therapy for Oral Cancer in a Murine Model, Cancer Research 56:1737–1741 (1996).

Kwong, Y.–L. et al., Combination Suicide and Cytokine Gene Therapy for Hepatic Metastases of Lung Cancer, Chest (in press submitted 1996 –copy enclosed).

Remesh, N. et al., High–Level Expression from a Cytomegalovirus Promoter in Macrophage Cells, Human Gene Therapy 6:1323–1327 (1995).

GENE THERAPY FOR SOLID TUMORS USING ADENOVIRAL VECTORS COMPRISING SUICIDE GENES AND CYTOKINE GENES

This application is a 371 of PCT/US94/09784 and a continuation-in-part of Ser. No. 08/112,745, filed Aug. 26, 1993, now U.S. Pat. No. 5,631,236.

BACKGROUND OF THE INVENTION

1. Field of the Invention

The present invention relates generally to the field of gene therapy. More particularly, the present invention relates to a novel gene therapy method of treating solid tumors, papillomas and warts using an adenoviral vector, a combination of adenoviral vectors, other viral vectors, and non-viral DNA transporter systems.

2. Description of the Related Art

Direct introduction of therapeutic genes into malignant cells in vivo can provide an effective treatment of localized tumors. Several novel treatment modalities have recently been attempted. For example, one treatment involves the delivery of normal tumor suppressor genes and/or inhibitors of activated oncogenes into tumor cells. A second treatment involves the enhancement of immunogeneity of tumor cells in vivo by the introduction of cytokine genes. A third treatment involves the introduction of genes that encode enzymes capable of conferring to the tumor cells sensitivity to chemotherapeutic agents. The herpes simplex virus-thymidine kinase (HSV-TK) gene can specifically convert a nucleoside analog (ganciclovir) into a toxic intermediate and cause death in dividing cells. It has recently been reported by Culver et al. (Science 256:1550–1552, 1992) that after delivery of the HSV-TK gene by retroviral transduction, subsequent ganciclovir treatment effectively caused brain tumor regression in laboratory animals. An attractive feature of this treatment modality for localized tumors is the so called "by-stander" effect. In the "by-stander" effect, the HSV-TK expressing tumor cells prevent the growth of adjacent non-transduced tumor cells in the presence of ganciclovir. Thus, not every tumor cell has to express HSV-TK for effective cancer treatment.

The HSV-TK retrovirus used by Culver et al., however, was limited by low viral titer. Thus, effective treatment of brain tumors necessitated the inoculation into animals of virus-producing cells rather than the viral isolate itself. Additionally, in previous experiments with synergeneic rats treated with a retrovirus and ganciclovir, the tumors were necrotic and were invaded by macrophages and lymphocytes. In Example 1, below, athymic mice were used and the tumor cells were destoyed without apparent involvement of the cellular immune response. The prior art remains deficient in the lack of an efficient gene therapy technique for the treatment of solid tumors.

SUMMARY OF THE INVENTION

An object of the present invention is a novel method of gene therapy in humans and animals.

An additional object of the present invention is a method of treating cancer by introducing an adenoviral vector encoding a protein capable of enzymatically converting a prodrug, i.e., a non-toxic compound into a toxic compound, and subsequently administering the prodrug.

A further object of the present invention is to provide a method for combination gene therapy using an-adenoviral vector with a "suicide gene", a protein capable of converting a prodrug; co-administered with a "cytokine gene", such as the interleukin-2 gene; and subsequently administering the prodrug.

Thus, in accomplishing the foregoing objects there is provided in accordance with one aspect of the present invention a method of treating a solid tumor, papilloma or warts in an animal or human, comprising steps of: introducing an adenoviral vector directly into solid tumor, that vector comprised of the following elements linked sequentially at appropriate distance for functional expression: a promoter, a 5' mRNA leader sequence, an initiation site, a nucleic acid cassette containing the suicide gene sequence to be expressed, a 3' untranslated region; and a polyadenylation signal; and administering a prodrug to animal or human, wherein prodrug is converted in vivo in to a toxic compound.

Further, in accomplishing the foregoing objects, there is provided in accordance with one aspect of the present invention a method of treating a solid tumor, papilloma or wart in an animal or human, comprising steps of: introducing an adenoviral vector directly into the solid tumor, that vector comprised of the following elements linked sequentially at appropriate distance for functional expression: a promoter, a 5' mRNA leader sequence, an initiation site, a nucleic acid cassette containing a suicide gene, a 3' untranslated region, and a polyadenylation signal; and at the same time introducing a second adenoviral vector, that vector comprised of the following elements linked sequentially at appropriate distance for functional expression: a promoter; a 5' mRNA leader sequence, an initiation site, a nucleic acid cassette containing a cytokine gene, a 3' untranslated region, and a polyadenylation signal; and administering a prodrug to animal or human, wherein prodrug is converted in vivo in to a toxic compound.

Other and further objects, features and advantages will be apparent from the following description of the presently preferred embodiments of the invention which are given for the purpose of disclosure when taken in conjunction with the accompanying drawings.

Figure 1:
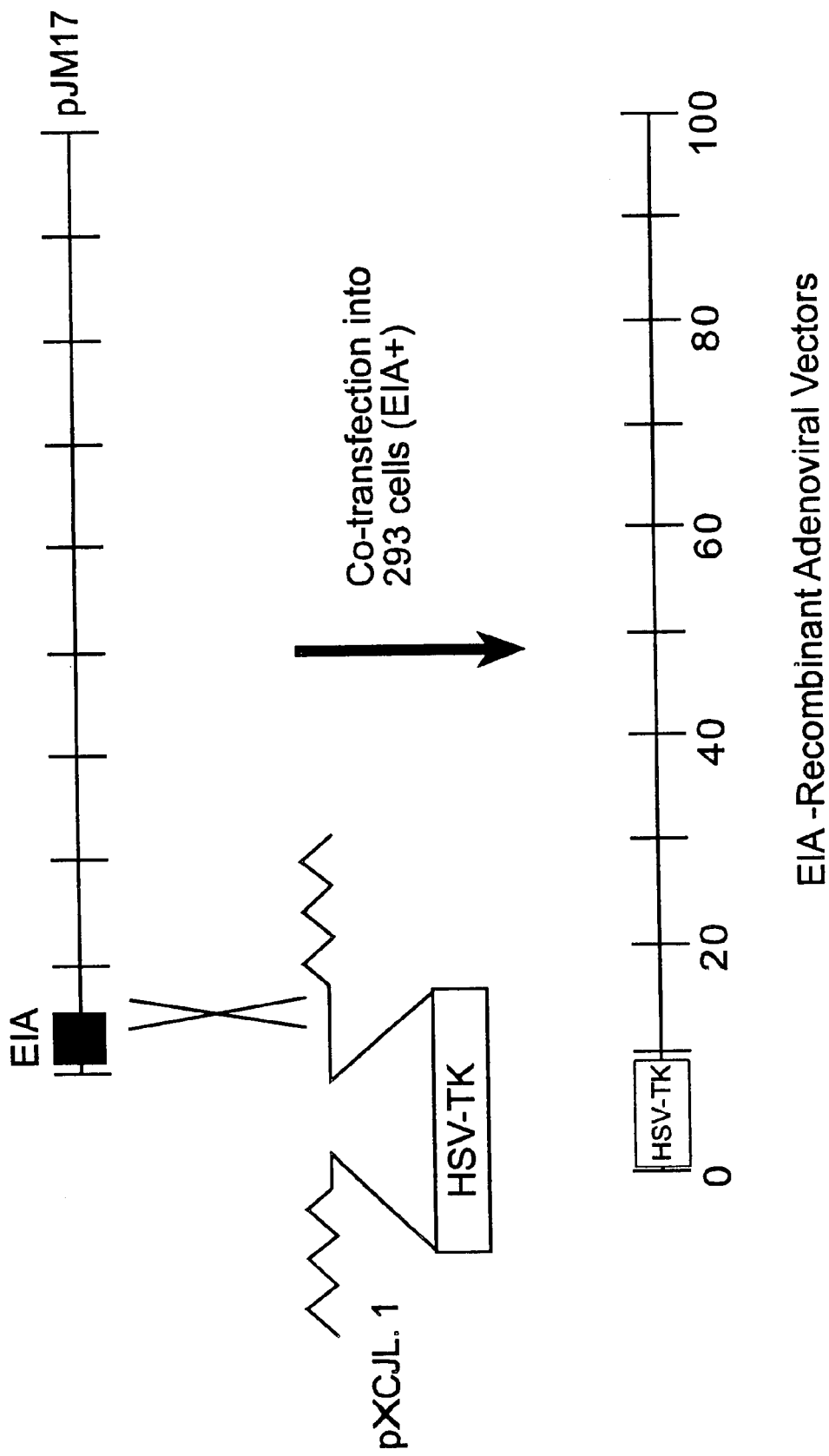
FIG. 1 shows a schematic representation of the construction of recombinant adenoviral vectors containing the herpes simplex virus thymidine kinase (HSV-TK) gene.
Figure 2A:
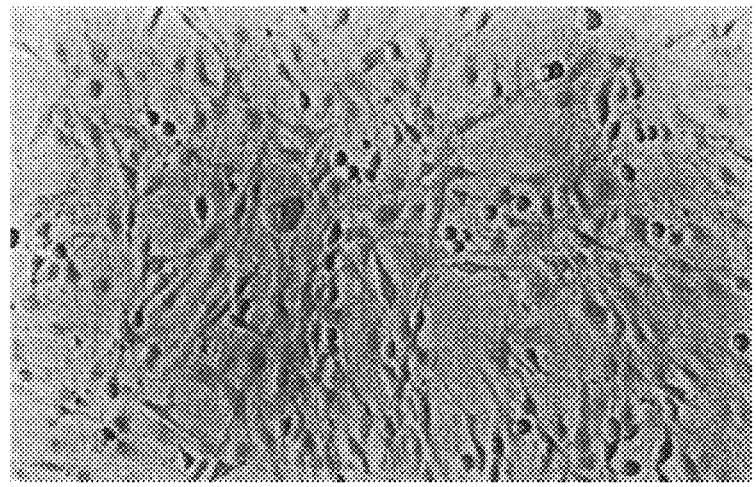
FIGS. 2(A–D) shows the efficient transduction of C6 glioma cells in vitro using a recombinant adenoviral vector containing the bacterial β-galactosidase gene (β-gal). Panel A: moi=O; Panel B: moi=125; Panel C: moi=500 and Panel D, moi=2,0000.
Figure 2B:
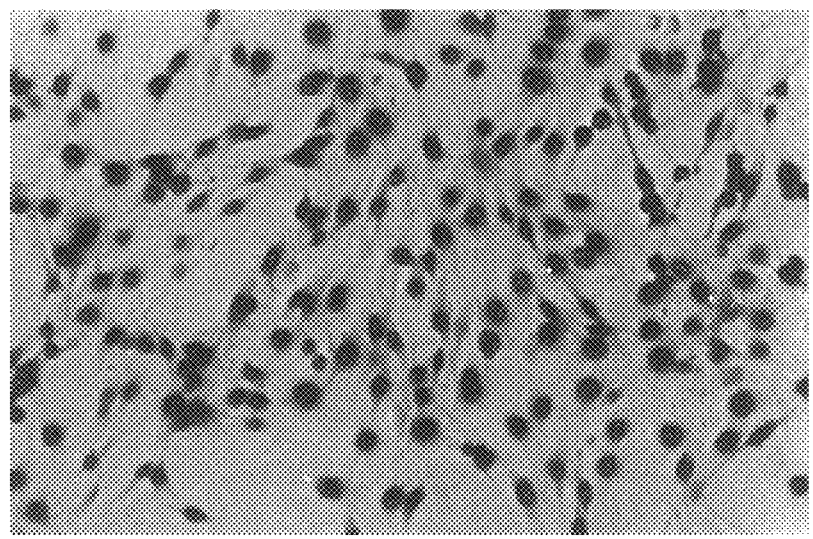
Figure 2C:
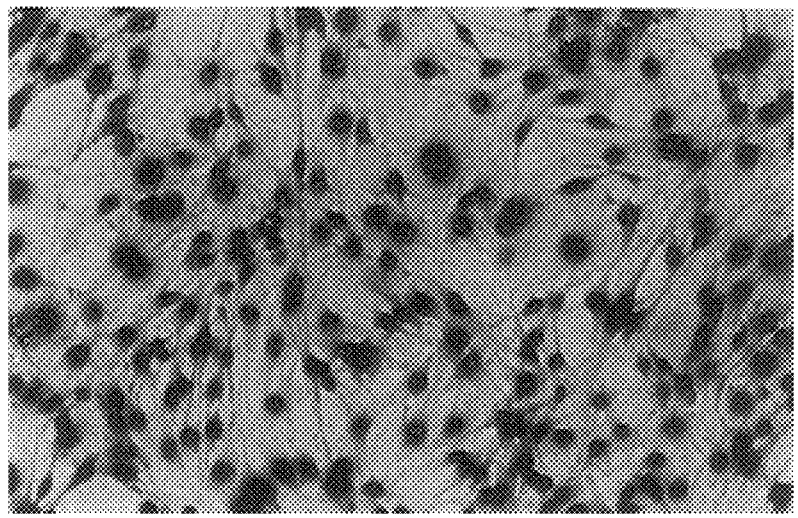
Figure 2D:

The drawings are not necessarily to scale. Certain features of the invention may be exaggerated in scale or shown in schematic form in the interest of clarity and conciseness.

DETAILED DESCRIPTION OF THE INVENTION

It will be readily apparent to one skilled in the art that various substitutions and modifications may be made to the invention disclosed herein without departing from the scope and spirit of the invention.

The term "vector " as used herein refers to a construction comprised of genetic material designed to direct transformation of a targeted cell. A vector contains multiple genetic elements positionally and sequentially oriented, i.e., operatively linked with other necessary elements such that the nucleic acid in a nucleic acid cassette can be transcribed and when necessary, translated in the transfected cells. In the present invention, the preferred vector comprises the following elements operatively linked for functional expression: a promoter, a 5' mRNA leader sequence, an initiation site, a nucleic acid cassette containing the sequence to be expressed, a 3' untranslated region, and a polyadenylation signal.

The term "stable transformation" as used herein refers to transformation in which the introduced therapeutic nucleic acid sequence (suicide gene) is, or the introduced therapeutic nucleic acid sequence and the cytokine sequence are, incorporated into the chromosomes of the whole cell. This leads to apparent stable change or transformation of a given characteristic of a cell.

The term "transformed" as used herein refers to a process for making or introducing a stable change in the characteristics (express phenotype) of a cell by the mechanism of gene transfer whereby DNA or RNA is introduced into a cell in a form where it expresses a specific gene product or alters an expression or affects endogenous gene products. The vector can be introduced into the cell by a variety of methods including microinjection, $CaPO_4$ precipitation, lipofection (liposome fusion), use of a gene gun and DNA vector transporter.

Recombinant adenoviruses containing the HSV-TK gene can be driven by various promoters including that of the cytomegalovirus, Rouse sarcoma virus LTR, murine leukemia virus LTR, simian virus 40 early and late, and endogenous HSV-TK genes. The recombinant adenoviruses are used to deliver efficiently the HSV-TK gene to tumors. Adenoviral vectors have several biological characteristics that make them more effective than retrovirus for somatic gene therapy of brain tumors. Adenoviral vectors have a broad host and cell range; multiple infection of host cells can produce high levels of gene expression; infection is episomal so that there is little possibility of insertional mutation of host genes; and high viral titers of up to $1 \times 10^{11}$ particles/ml can be produced.

A wide variety of cancer, papillomas and warts can be treated by the same therapeutic strategy. Representative examples include colon carcinoma, prostate cancer, breast cancer, lung cancer, skin cancer, liver cancer, bone cancer, ovary cancer, pancreas cancer, brain cancer, head and neck cancer, lymphoma and other solid tumors. Representative examples of papillomas include squamous cell papilloma, choroid plexus papilloma and laryngeal papilloma. Representative examples of wart conditions include genital warts, plantar warts, epidermodysplasia verruciformis and malignant warts.

The term "nucleic acid cassette" as used herein refers to the genetic material of interest which can express a protein, or a peptide, or RNA. The nucleic acid cassette is operatively linked i.e., positionally and sequentially oriented in a vector, with other necessary elements such that the nucleic acid in the cassette can be transcribed and, when necessary, translated.

The present invention provides a method of treating a localized solid tumor, papilloma or wart in an animal or human, comprising steps of: introducing an adenoviral vector directly into said tumor or papilloma, comprised of the following elements linked sequentially at appropriate distance for functional expression: a promoter, a 5' mRNA leader sequence, an initiation site, a nucleic acid cassette containing the sequence to be expressed, a 3' untranslated region, and a polyadenylation signal; and administering a prodrug to animal or human, wherein prodrug is converted in vivo into a toxic compound.

Another aspect of the present invention provides a method of treating solid tumors, papillomas or warts in an animal or human, comprising steps of: introducing an adenoviral vector directly into solid tumor, that vector comprised of the following elements linked sequentially at appropriate distance for functional expression: a promoter, a 5' mRNA leader sequence, an initiation site, a nucleic acid cassette containing a suicide gene, a 3' untranslated region, and a polyadenylation signal; and at the same time introducing a second adenoviral vector, that vector comprised of the following elements linked sequentially at appropriate distance for functional expression: a promoter, a 5' mRNA leader sequence, an initiation site, a nucleic acid cassette containing a cytokine gene, a 3' untranslated region, and a polyadenylation signal; and administering a prodrug to animal or human, wherein prodrug is converted in vivo into a toxic compound.

In addition to adenoviral vectors, other delivery systems may be used, either viral or non-viral. A targeted system for non-viral forms of DNA or RNA requires four components: 1) the DNA or RNA or interest; 2) a moiety that recognizes and binds to a cell surface receptor or antigen; 3) a DNA binding moiety; and 4) a lytic moiety that enables the transport of the complex from the cell surface to the cytoplasm. Examples of such non-viral transfer systems may be found in Smith and Woo, U.S. Ser. No. 07/855,389, filed Mar. 20, 1992. Further, liposomes and cationic lipids can be used to deliver the therapeutic gene combinations to achieve the same effect. Potential viral vectors include expression vectors derived from viruses such as vaccinia virus, herpes virus, and bovine papilloma virus. In addition, episomal vectors may be employed. Other DNA vectors and transporter systems are known in the art. Currently, the preferred embodiment envisions the use of an adenovirus system.

In the method of the present invention, the therapeutic nucleic acid sequence or "suicide gene" is a nucleic acid coding for a product, wherein the product causes cell death by itself or in the presence of other compounds. A representative example of such a therapeutic nucleic acid (suicide gene) is one which codes for thymidine kinase of herpes simplex virus. Additional examples are thymidine kinase of varicella zoster virus and the bacterial gene cytosine deaminase which can convert 5-fluorocytosine to the highly toxic compound 5-fluorouracil.

As used herein "prodrug" means any compound useful in the methods of the present invention that can be converted to a toxic product, i.e. toxic to tumor cells. The prodrug is converted to a toxic product by the gene product of the therapeutic nucleic acid sequence (suicide gene) in the vector useful in the method of the present invention. Representative examples of such a prodrug is ganciclovir which is converted in vivo to a toxic compound by HSV-thymidine kinase. The ganciclovir derivative subsequently is toxic to tumor cells. Other representative examples of prodrugs include acyclovir, FIAU [1-(2-deoxy-2-fluoro-β-D-arabinofuranosyl)-5-iodouracil], 6-methoxypurine arabinoside for VZV-TK, and 5-fluorocytosine for cytosine deambinase.

Ganciclovir may be administered readily by a person having ordinary skill in this art. A person with ordinary skill would readily be able to determine the most appropriate dose and route for the administration of ganciclovir. Preferably, ganciclovir is administered in a dose of from about 1–20 mg/day/kg body weight. Preferably, acyclovir is administered in a dose of from about 1–100 mg/day/kg body weight and FIAU is administered in a dose of from about 1–50 mg/day/kg body weight.

In another method of the present invention, an adenovirus containing a cytokine gene sequence can be driven by various promoters including Rous Sarcoma Virus-Long Terminal Repeat, cytomegalovirus promoter, murine leukemia virus LTR, simian virus 40 early and late promoters, and herpes simplex virus thymidine kinase. This cytokine gene-containing adenovirus can then be co-administered with the suicide gene-containing adenovirus, to effect a "combination gene therapy."

As used herein, "cytokine gene" means a gene encoding any one of the soluble subtances produced by lymphoid or non-lymphoid cells characterized by their ability to respond to anitgen invasion. This includes the inferons and factors involved in the stimulation of helper and cytolytic T-lymphocytes to mount an effective anti-tumoral response, as well as macrophages and monocytes to assist in the activation of B-lymphocytes to antibody-producing cells. Cytokine genes include interleukin-1, interleukin-2, interleukin-4, interleukin-6, interleukin-7, interleukin-10, interleukin-12, interferon-α, interferon-β, interferon-δ, tumor necrosis factor α and β, granulocyte-macrophage colony stimulating factor (GM-CSF) and granulocyte colony stimulating factor (G-CSF).

Abbreiviations used herein include: ADV/RSV-TK, a recombinant vector containing the thymidine kinase gene driven by the Rous Sarcoma Virus long terminal repeat; ADV/RSV-β-gal, the same vector as above but containing the gene for β-galactosidase; TK, Herpes simplex virus thymidine kinase gene; GCV, ganciclovir; PBS, phospho-buffered saline.

The following examples are offered by way of illustration and are not intended to limit the invention in any manner.

EXAMPLE 1

Gene therapy for brain tumors: Regression of experimental gliomas by adenovirus-mediated gene transfer in vivo.

Construction of the adenoviral vector.

The construction of recombinant adenoviral vectors containing the herpes simplex virus-thymidine kinase (HSV-TK) gene (Summers, W. C., et al. at PNAS 78(3), pp. 1441–1445 (1981)) is shown in FIG. 1. Three different vectors were constructed, each with a different promoter inserted 5' to the coding sequence and polyadenylation signal of the HSV-TK gene: (1) the long terminal repeat sequence of the Rous Sarcoma Virus (Ad/RSV-TK); (2) the early gene promoter of the cytomegalovirus (Ad/CMV-TK); and (3) the thymidine kinase gene promoter of herpes simplex virus (Ad/HSV-TK).

Transduction of C6 Glioma cell.

Transduction of C6 glioma cells in vitro was accomplished using a recombinant adenoviral vector containing the bacterial B-galactosidase gene. $5 \times 10^5$ C6 cells were plated on 1.5 cm diameter wells and transduced with AdV/RSV-B-gal at various viral doses and stained with X-gal two days later. Panel A illustrates the results using an moi of O. Panel B shows the results using an moi of 125. Panel C illustrates the results using an moi of 500 and Panel D shows the results when an moi of 2,000 was used.

Transduction of C6 cells usinz the HSV-TK gene.

Transduction of C6 glioma cells was also accomplished using a recombinant adenoviral vector containing the HSV-TK gene (Ad/RSV-TK). $5 \times 10^5$ C6 cells were plated on 1.5 cm diameter wells and transduced with the viral vector at different doses as indicated. Cells were harvested two days later and protein extracts prepared. The HSV-TK enzymatic activity was d e termined by phosphorylation of $^3$H-acyclovir as described in James, et al., *J. Biol. Chem.*, 253 (24):8721–8727 (1978).

Figure 3:
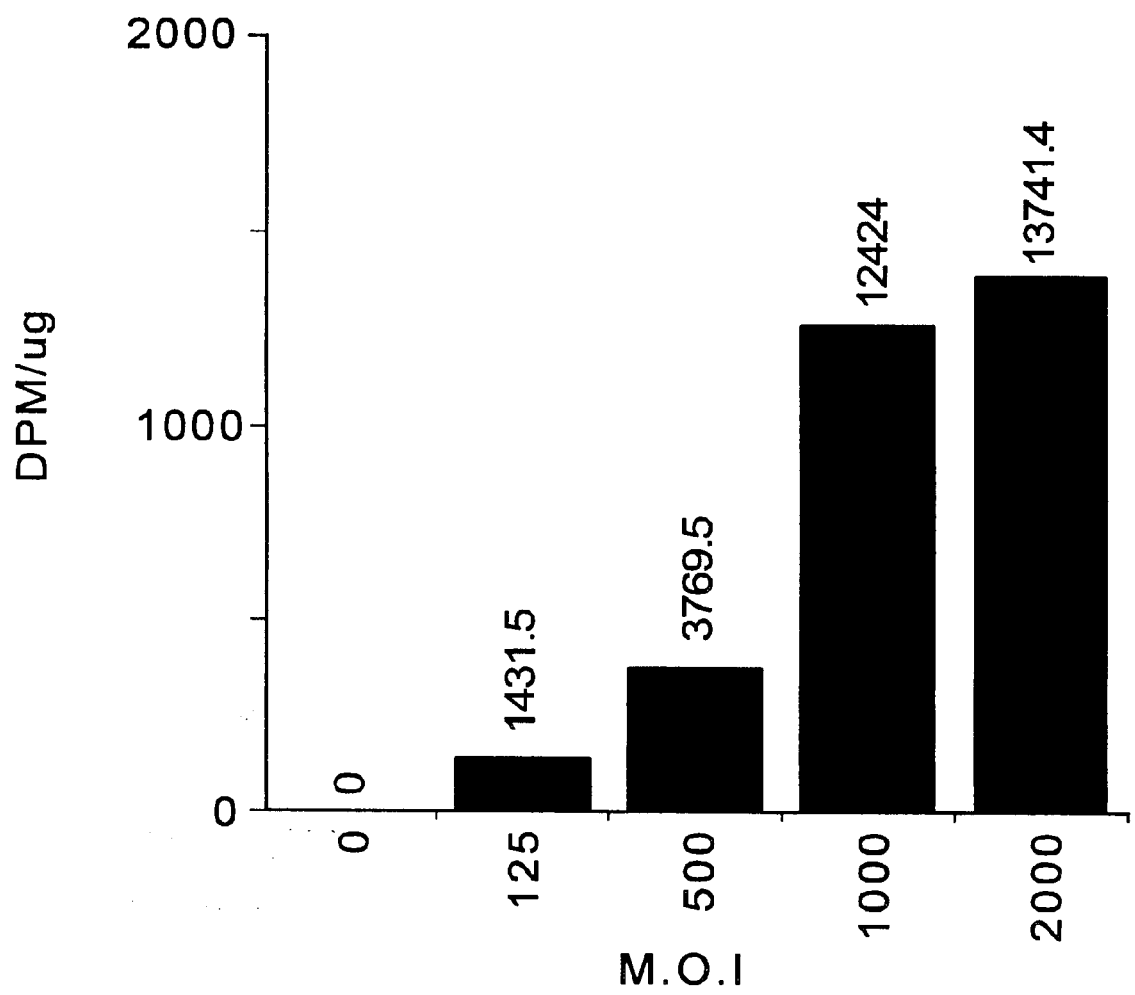
FIG. 3 shows HSV-TK enzymatic activity in C6 glioma cells after transduction with a recombinant adenoviral vector containing the HSV-TK gene.

As can be seen from FIG. 3, HSV-TK activity was highest in C6 cells after transduction with AD/RSV-TK having an m.o.i. of 1000 and 2000, respectively.

Ganciclovir susceptibility of HSV-TK$^+$ C6 cells.

Figure 4:
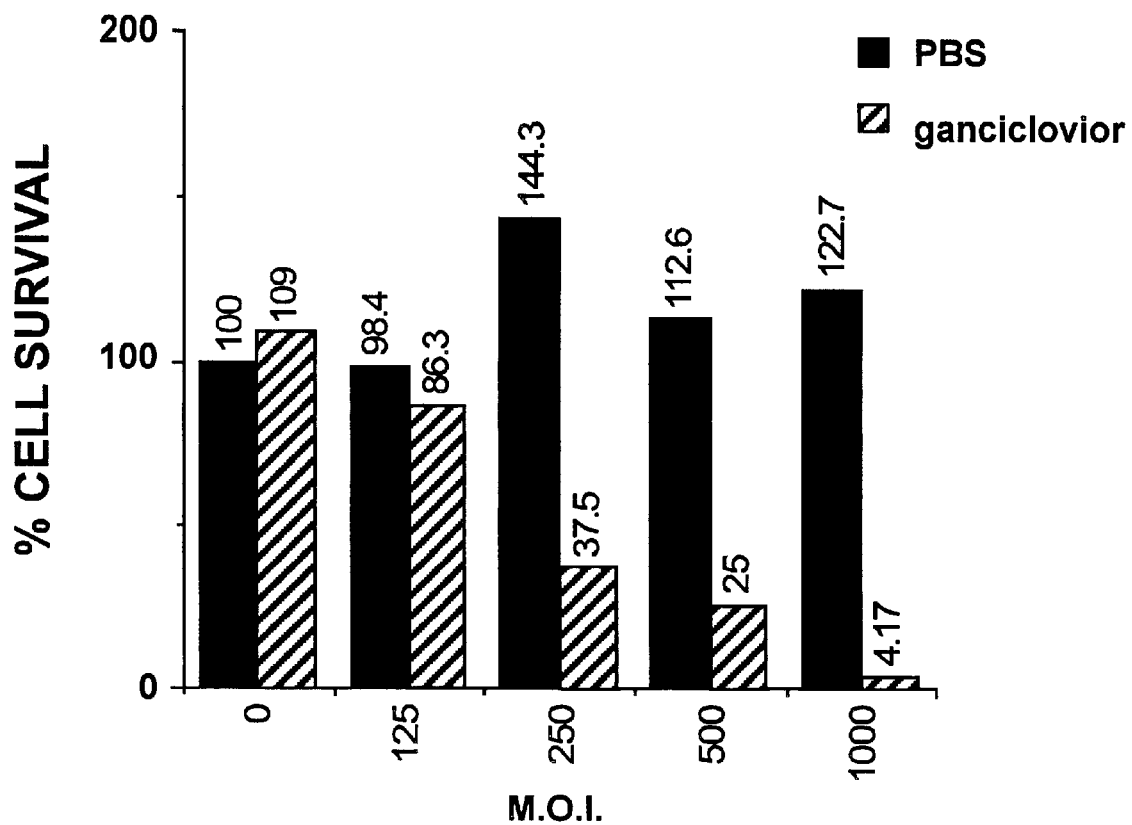
FIG. 4 shows the susceptibility to ganciclovir toxicity of Ad/RSV-TK transduced C6 glioma cells in vitro.

The susceptibility to ganciclovir toxicity of Ad/RSV-TK transduced C6 glioma cells is shown in FIG. 4. Duplicate plates of viral transduced cells in FIG. 3 were subjected to ganciclovir treatment at 2 ug/ml and the number of survival cells was counted at 72 hours.

FIG. 4 illustrates the effect of ganciclovir in C6 cells after transduction with AD/RSV-TK. FIG. 4 shows that an m.o.i. of 250 produced a cell kill of 62.5%; and m.o.i. of 500 resulted in a cell kill of 75%. Most dramatically, an m.o.i. of 1000 resulted in a cell kill of approximately 95%.

Gene therapy strategy.

Figure 5:
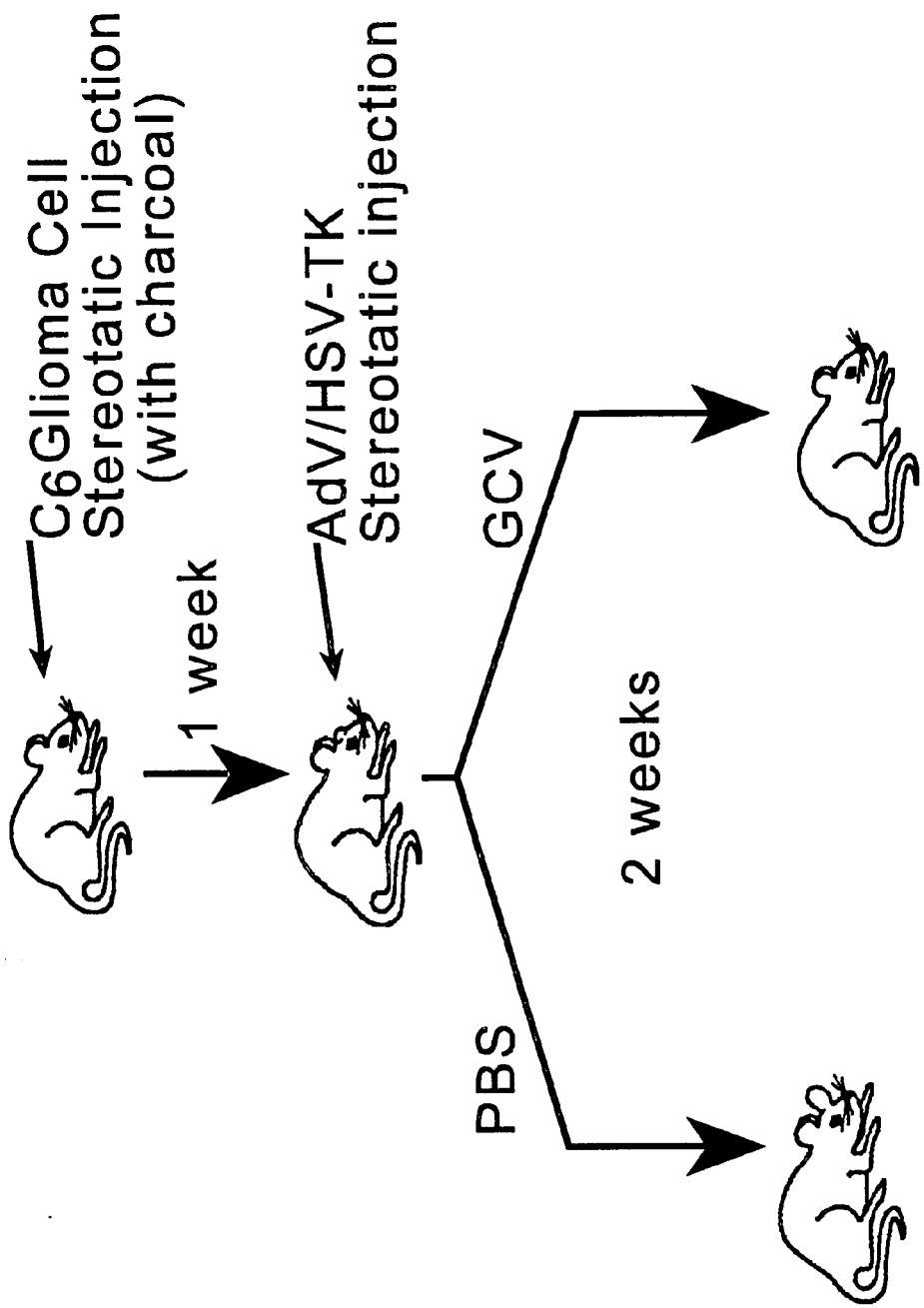
FIG. 5 shows the strategy for gene therapy of brain tumors using recombinant adenoviral vectors containing HSV-TK.
Figure 6:
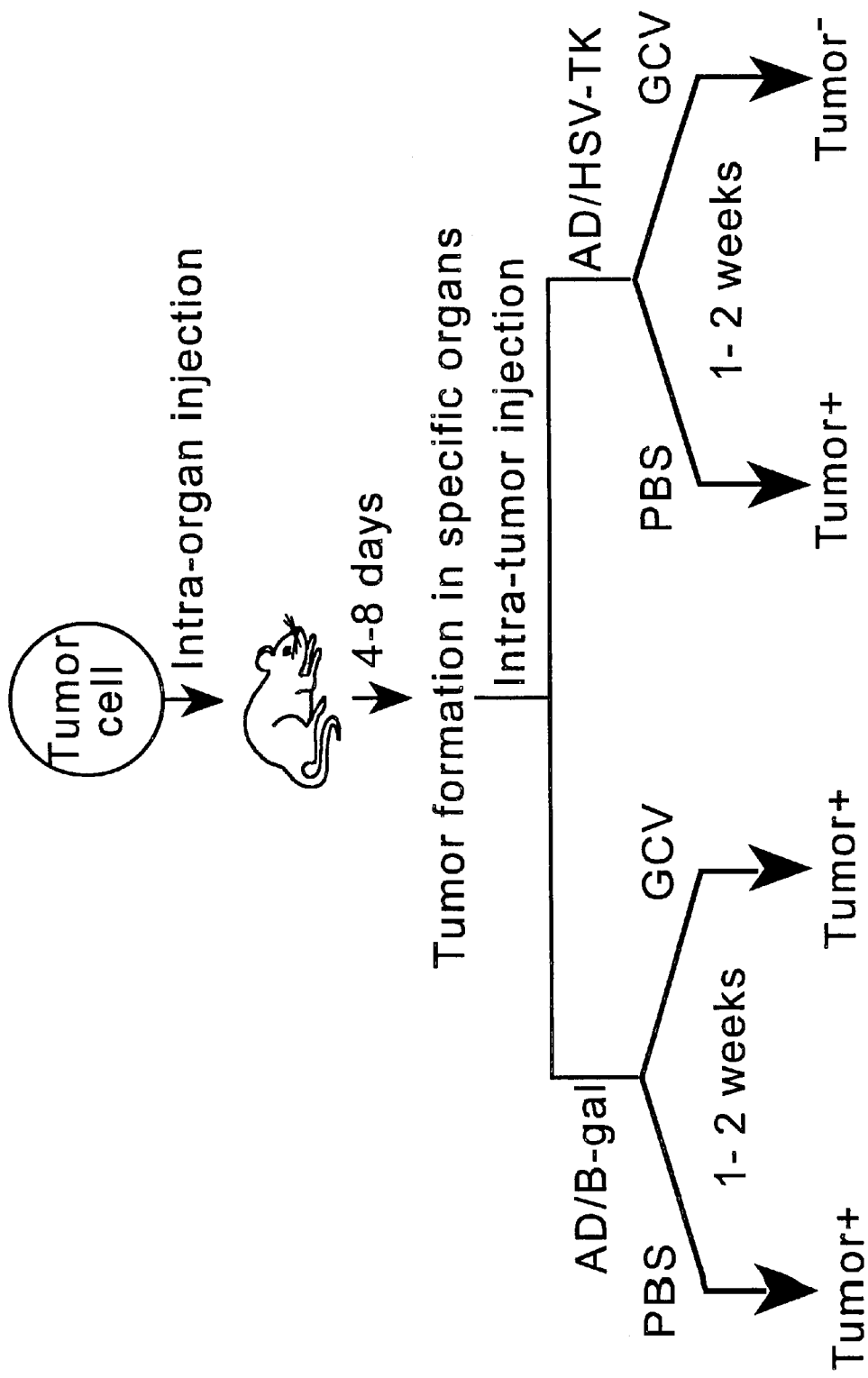
FIG. 6 shows a strategy for gene therapy of a generic solid tumor.

The strategy for gene therapy of brain cancer using recombinant adenoviral vectors containing HSV-TK is shown in FIGS. 5 and 6. In FIG. 5, C6 glioma cells were injected stereotactically into nude mouse brain with a little charcoal to mark the site of injection. About 1 week later, Ad/RSV-TK was injected into the tumor stereotactically. The mice were then divided into 2 groups, one treated with ganciclovir for 6 days and the other with phosphate-buffered saline (PBS). The animals were then kept without further treatment until tumors developed, i.e., about one to two weeks.

FIG. 6 shows intra-organ injections of tumor cells into mice. After 4–8 days, the mice were divided into two groups. In one group AD/β-gal was injected into the tumor and in the other group AD/HSV-TK was injected into the tumor. After about 1–2 weeks, half the mice in each group were treated with PBS and the other half were treated with ganciclovir. Only the mice treated with ganciclovir and AD/HSV-TK showed tumor regression.

Effect of Ad/RSV-TK injection and Ganciclovir on brain tumors.

Experimental animals were inoculated with $10^4$ C6 glioma cells by stereotactic injection into the brain. After 4–8 days, $3 \times 10^8$ particles of recombinant adenoviral vector containing the HSV-TK (Ad/RSV-TK) gene were stereotactically injected into the same site. Twelve hours later, the animals were treated daily either by intraperitoneal administration with buffer (PBS) or Ganciclovir (GCV:125 mg/kg) for 6 consecutive days. The animals were kept without further treatment until the 20th day from the day of tumor cell inoculation and the appearance of brain tumors for individual animals was recorded.

Figure 7:
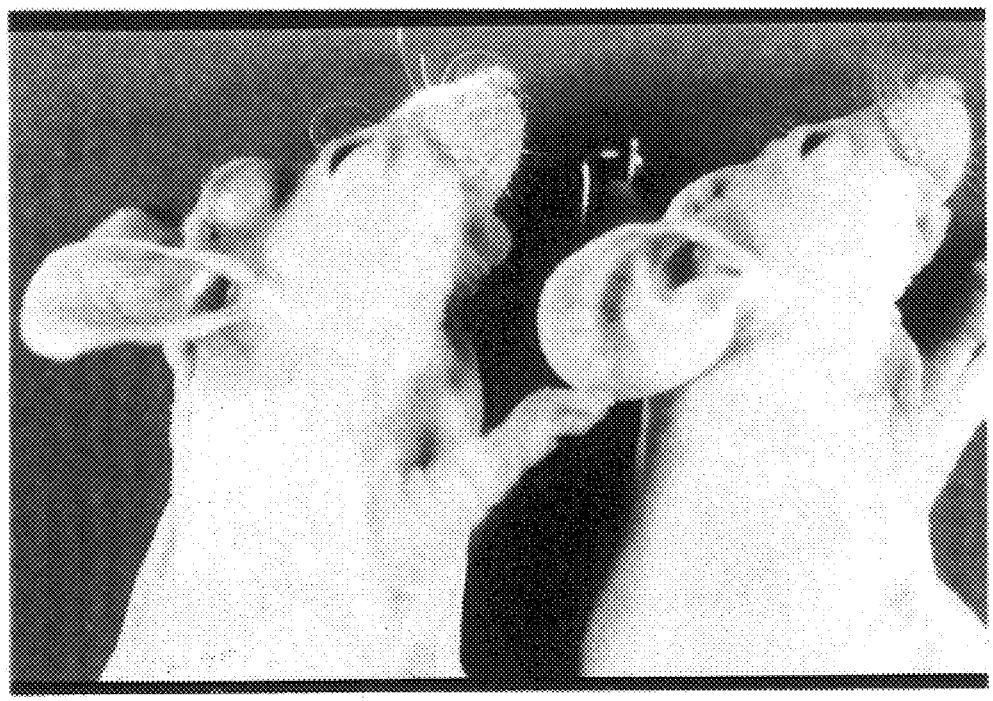
FIG. 7 shows experimental animals at 20 days post C6 Glioma cell inoculation into the brain, followed by stereotactic Ad/RSV-TK administration. The left animal was treated with PBS and the right animal treated with ganciclovir.

FIG. 7 shows experimental animals at 20 days post C6 glioma cell inoculation into the brain followed by stereotactic Ad/RSV-TK administration. A representative PBS-treated animal with obvious brain tumor is shown on the left panel of FIG. 7 and a representative GCV-treated mouse without obvious brain tumor is shown on the right panel of FIG. 7.

Gross anatomy of mouse brains with and without tumor.

Figure 8:
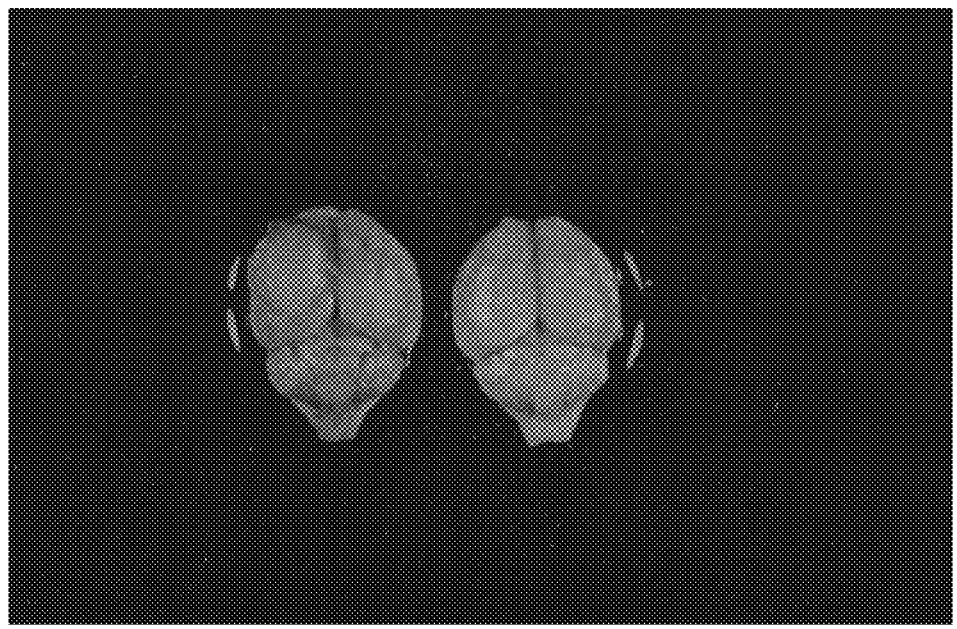
FIG. 8 shows whole brain of mice as described in FIG. 7 after either PBS treatment (left) or ganciclovir treatment (right).

FIG. 8 shows whole brains of mice after either PBS treatment (left) or ganciclovir treatment (right) as described in Example 6. The brains were obtained from experimental animals at 20 days after tumor cell inoculation as described above. The tumor mass in PBS treated mice was dissected from the brain and placed on top of the organ. Furthermore, because the C6 glioma cells were originally injected into mouse brain with a little charcoal, the ganciclovir treated mouse brain has a spec of charcoal which demonstrates the site of tumor cell injection.

TABLE I

Brain Tumor Treatment with an Adenoviral Vector having the HSV-TK Gene

| TREATMENT | PBS | GGV |
|---|---|---|
| Number of Treated Animals | 4 | 4 |
| Number of Animals with Brain Tumor | 4 | 1 |

EXAMPLE 2

Effect of ganciclovir on a breast cancer cell line.
Treatment of localized breast cancer tumors in mice.

The "by-stander" effect in solid tumors was examined using a breast cancer cell line (MOD) derived from BALB/c mouse. This cell line easily forms localized tumors by subcutaneous injection of tumor cells into congenic recipients. Thus, this cell line can be used as a model for gene therapy for breast cancer.

Figure 9:
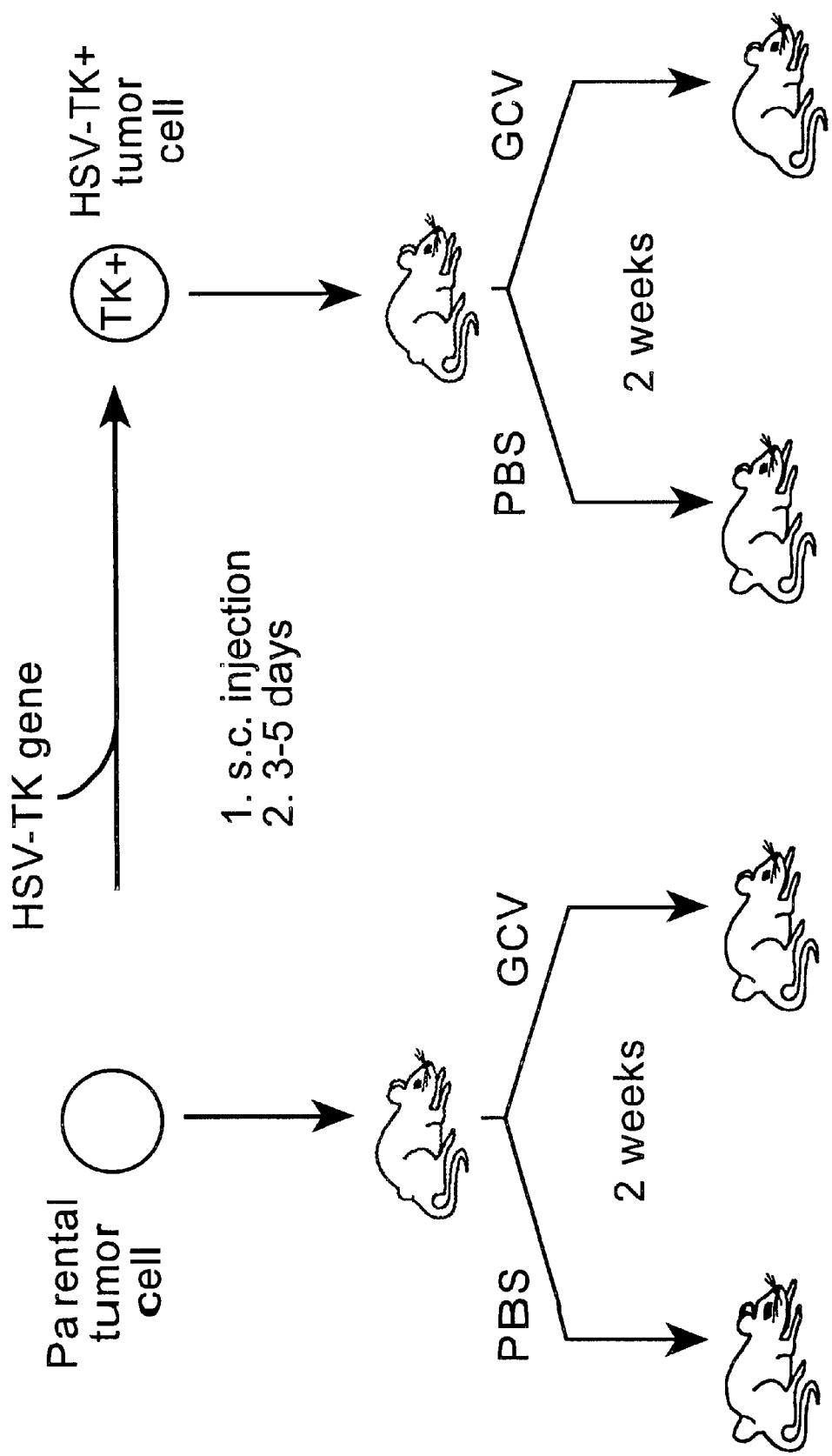
FIG. 9 shows a schematic of the effect of ganciclovir treatment and HSV-TK$^+$ breast tumor (MOD) regression.

FIG. 9 is a schematic of the effect of ganciclovir treatment and HSV-TK$^+$ tumor regression. FIG. 9 shows that, in one case, the parental tumor cells were injected subcutaneously in mice. The mice were divided into two groups. One group was treated with PBS; the other group was treated with GCV for 5 days. Two weeks later, the animals were sacrificed. FIG. 9 also shows that another group of mice were injected with tumor cells into which the HSV-TK gene was inserted in vitro (HSV-TK$^+$). Subsequently, the mice were treated with either PBS or GCV as described above.

Figure 10A:
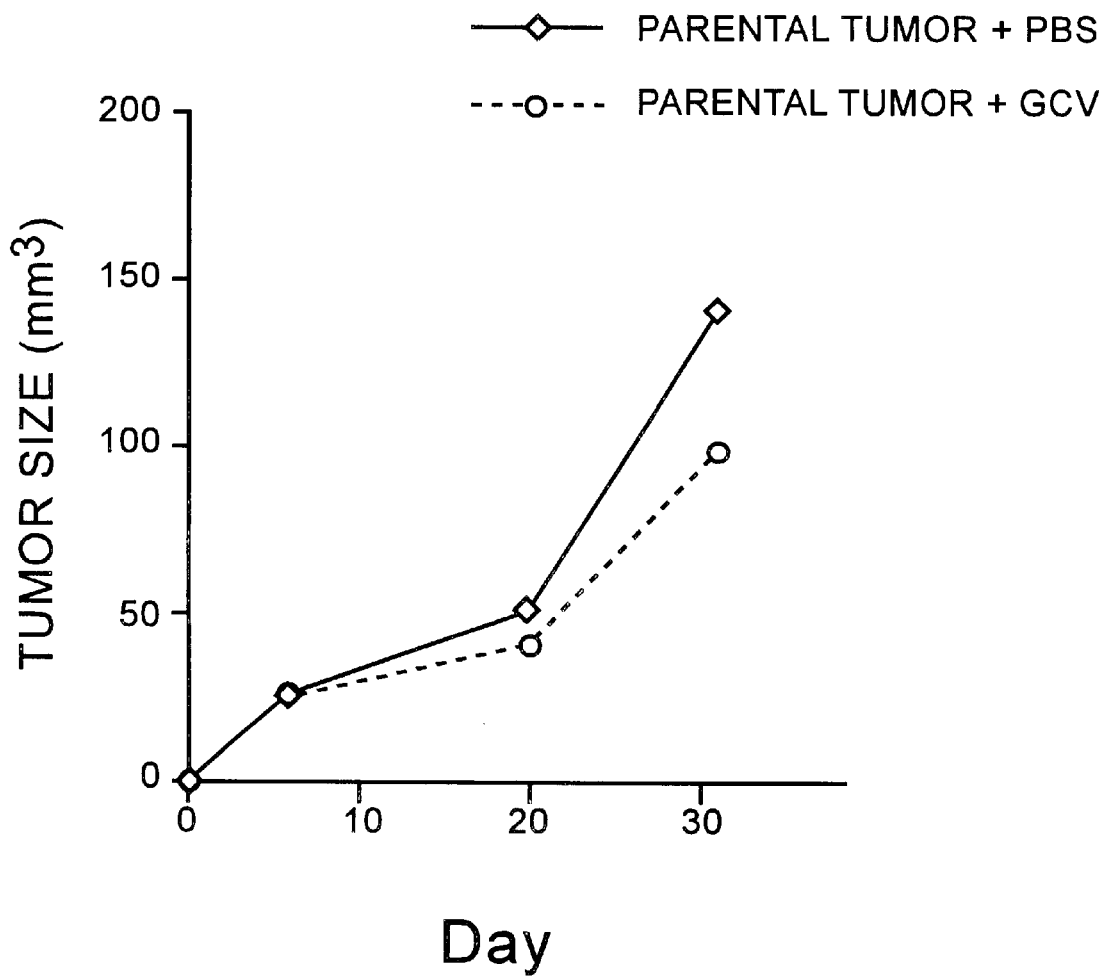
FIG. 10 shows the effect of ganciclovir treatment on HSV-TK$^+$ breast tumor (MOD) size.
Figure 10B:
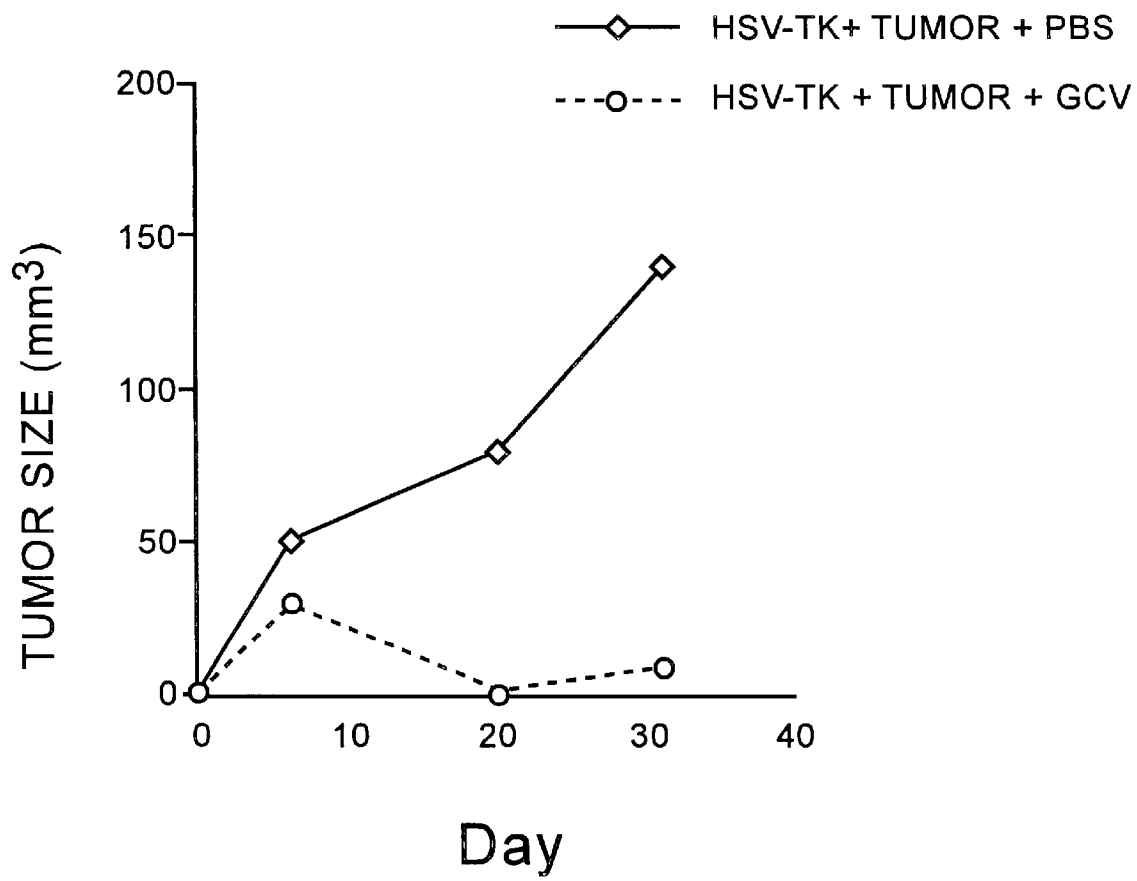

FIG. 10 shows the effect of ganciclovir treatment on tumor size. The top panel shows that there was little significant difference between treatment with PBS or GCV in mice injected with the parental cells alone. The bottom panel of FIG. 10 shows that ganciclovir treatment significantly reduced tumor size when the HSV-TK gene had been inserted into the tumor cells prior to injection into the mice.

Figure 11:
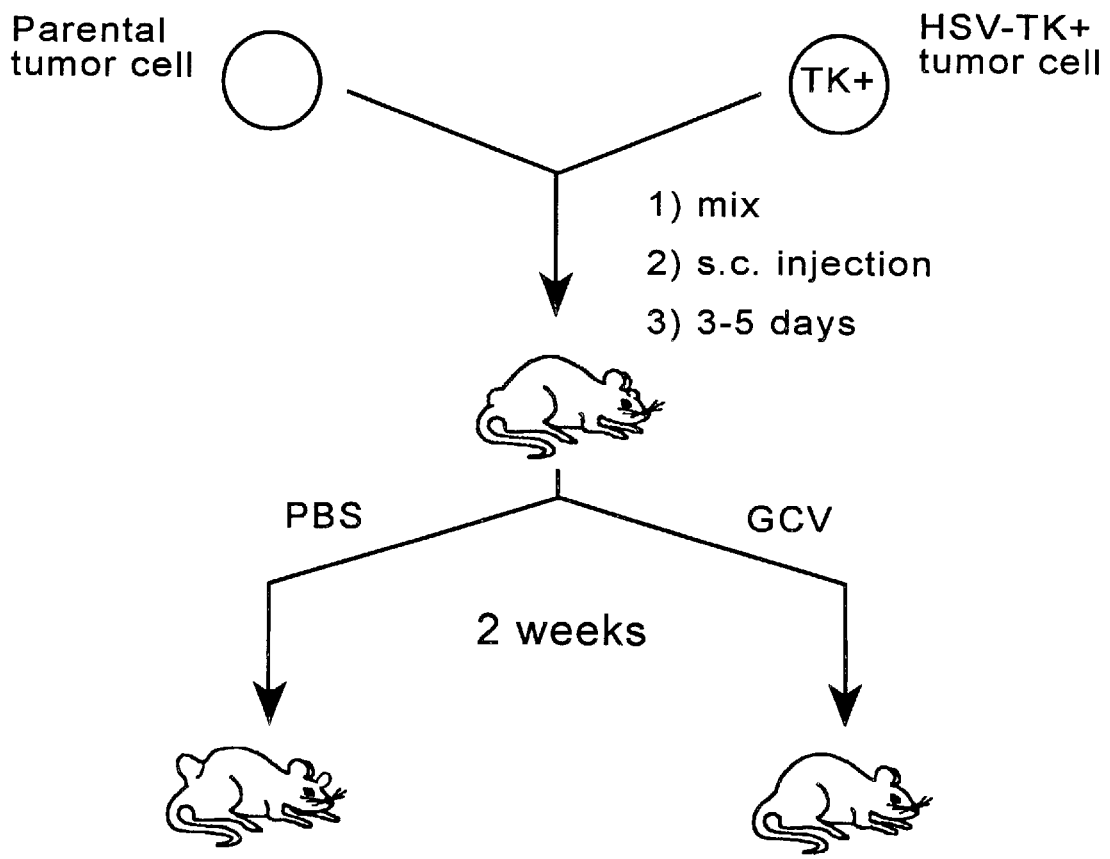
FIG. 11 shows a schematic of the bystander effect when parental breast tumor (MOD) cells and tumor cells containing the HSV-TK gene were mixed and injected subcutaneously into mice.

FIG. 11 shows a schematic of the bystander effect. In the schematic of FIG. 11, parental tumor cells and tumor cell containing the HSV-TK gene were mixed and injected subcutaneously into mice. The mice were then treated with either PBS or GCV.

Results

Figure 12:
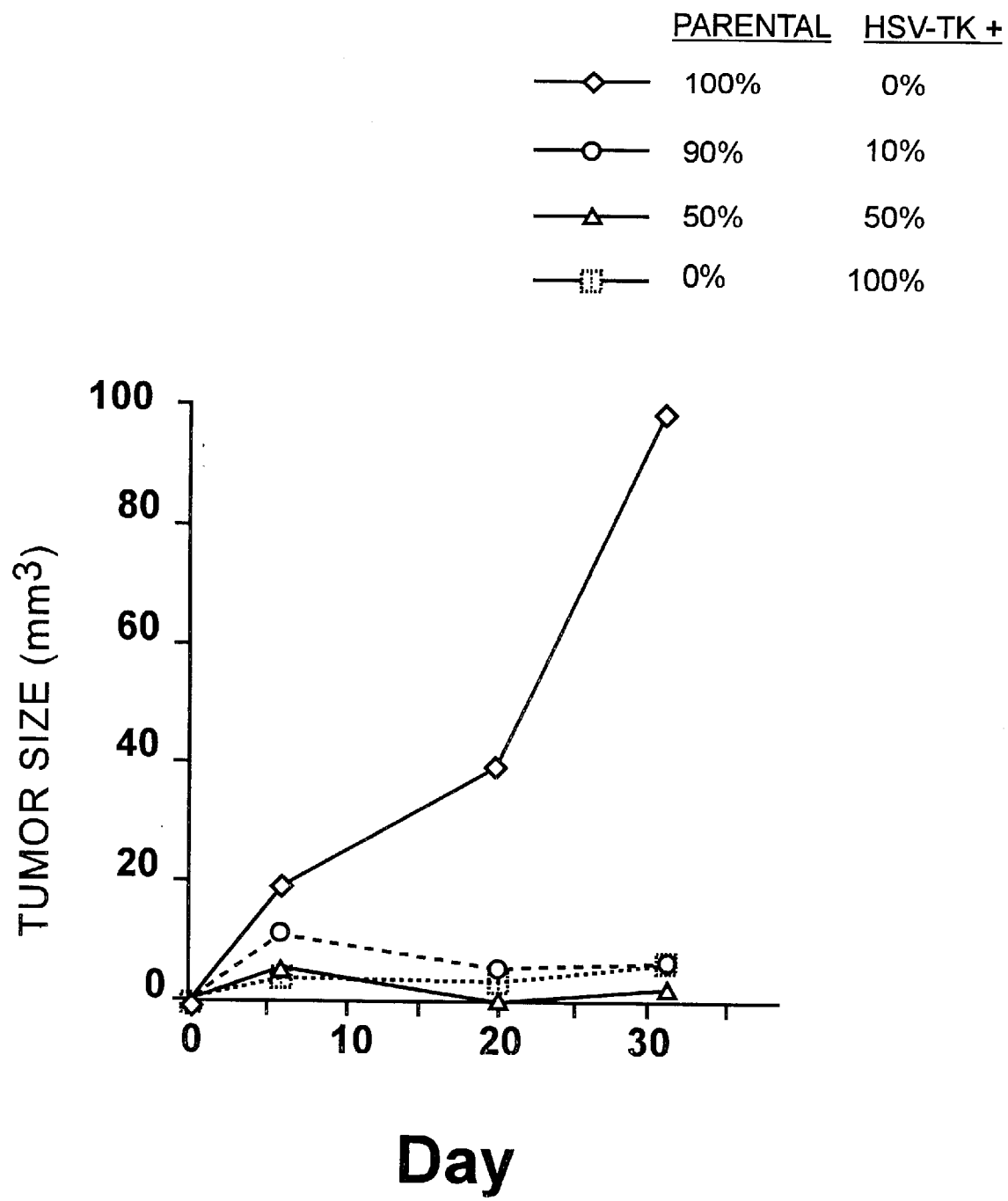
FIG. 12 shows the effect of PBS or ganciclovir on tumor size when mice had been treated with either 100% parental tumor cells, 100% HSV-TK containing tumor cells, 90% parental/10% HSV-TK tumor cells or 50% parental/50% HSV-TK breast tumor (MOD) cells.

HSV-TK gene transformed MOD cells in vitro exhibited greatly enhanced sensitivity to the toxic effects of ganciclovir over the parental tumor cells. When tested in vivo, not only the growth of HSV-TK gene transformed MOD cells were inhibited by intraperitoneal administration of ganciclovir but the sold tumors also regressed in mice. Regression, however, was not observed with tumors derived purely from the parental tumor cells. More importantly, a strong "by-stander" effect in the breast tumor cells in vivo was also observed. When animals were co-injected with the HSV-TK expressing MOD cells and the parental tumor cells, as few as 10% of HSV-TK expressing cells was sufficient to inhibit overall tumor growth in the animals after ganciclovir treatment (FIG. 12). In this set of animals however, the tumors recurred after 30–45 days. On the other hand, animals inoculated with 90% or 50% TK$^+$ cells remained tumor free during this period.

Cell-type specificity of HSV-TK gene expression after recombinant adenoviral vector administration in a particular solid tumor, papilloma or wart can also be achieved with the use of tissue-specific promoters to direct the transcription of the HSV-TK gene. Some examples of the various tissue specific promoters are shown in Table II.

TABLE II

| TUMOR | PROMOTERS |
|---|---|
| liver | albumin, alpha-fetoprotein, $\alpha_1$-antitrypsin, transferrin transthyretin |
| colon | carbonic anhydrase I, carcinoembrogen's antigen |
| ovary, placenta | estrogen, aromatase cytochrome P450, cholesterol side chain cleavage P450, 17 alpha-hydroxylase P450 |
| prostate | prostate specific antigen, gp91-phox gene, prostate-specific kallikrein (hKLK2) |
| breast, G.I. | erb-B2, erb-B3, β-casein, β-lactoglobulin, WAB (whey acidic protein) |
| lung | surfactant protein C Uroglobin (cc-10, CIIacell 10 kd protein) |
| skin | K-14-keratin, human keratin 1 or 6, loicrin |
| brain | glial fibrillary acidic protein, mature astrocyte specific protein, myelin, tyrosine hydroxylase |
| pancreas | villin, glucagon, Insulin Islet amyloid polypeptide (amylin) |
| thyroid | thyroglobulin, calcitonin |
| bone | Alpha 1 (I) collagen, osteocalcin, bone sialoglycoprotein |
| kidney | renin, liver/bone/kidney alkaline phosphatase, erythropoietin (epo) |

EXAMPLE 3

Adenovirus-mediated Gene Therapy of experimental gliomas.

The efficacy of adenoviral-mediated gene therapy to treat brain tumors was shown in a syngeneic glioma model. Tumor cells were transduced in situ with a replication-defective adenovirus (ADV) carrying the herpes simplex virus thymidine kinase gene (HSV-tk) controlled by the Rous sarcoma virus promoter. Expression of the HSV-tk gene enables the transduced cell to convert the drug ganciclovir to a form that is cytotoxic to dividing cells. Tumors were generated in Fischer 344 rats by stereotaxic implantation of 9L gliosarcoma cells into the caudate nucleus. Eight days later, the tumors were injected either with the ADV carrying the HSV-tk gene (ADV-tk) or a control ADV vector containing the β-galactosidase gene (ADV-βgal) and the rats were treated with either ganciclovir or with saline. Tumor size was measured 20 days after implantation of 9L cells or at death. Rats treated with ADV-βgal and ganciclovir or with ADV-tk and saline had large tumors. No tumors were detected in animals treated with ADV-tk and with ganciclovir at doses $\geq 80$ mg/kg. An infiltrate of macrophages and lymphocytes at the injection site in animals treated with ADV-tk and ganciclovir indicated an active local immune reaction. In survival studies, all animals treated with ADV-tk and ganciclovir have remained alive longer than 80 and up to 120 days after tumor induction, whereas all untreated animals died by 22 days. These results demonstrate that adenovirus-mediated transfer of HSV-tk to glioma cells in vivo confers sensitivity to ganciclovir, and represents a method of treatment of brain tumors.

Adenoviral Constructs.

ADV-tk vector was prepared by inserting HSV-tk into the plasmid which contained the Rous sarcoma virus long-terminal-repeat promoter (RSV-LTR) to generate pADL.1/RSV-tk (Chen et al., 1994). Recombinant adenovirus was produced by co-transfecting 293 cells with pADL.1/RSV-tk and a plasmid, pJM17, containing the adenovirus genome.

The 293 cells are transformed human kidney cells the E1 region of the adenovirus genome. When 293 cells were co-transfected with pADL.1/RSV-tk and pJM17, replication-defective adenovirus was by homologous recombination (Graham and Prevec, 1991). Virus titer was determined by optical absorbance at 260 nm. A replication-deficient adenovirus vector carrying the *E. coli* β-galactosidase gene under control of the RSV-LTR (ADV-βgal) was used as a control vector.

Experimental Tumor Generation.

In vivo the 9L tumor cells exhibit morphology described as mixed glioblastoma and sarcoma, or gliosarcoma (Barker et al., 1973; Weizaecker et al., 1981). The 9L glioma cells were maintained in Dulbecco's modified Eagle medium (DMEM) supplemented with 10% fetal bovine serum, penicillin (100 U/ml), and streptomycin (100 μg/ml) in 5% $CO_2$ at 37° C. The tumor cells were harvested for injection by treating the cells at 37° C. with 0.25% trypsin in 1.0 mM ethylenediamine tetra-acetic acid for 5 minutes. The cells were collected in DMEM, washed, and resuspended in Hanks' balanced salt solution (HBSS) at a concentration of $2.0 \times 10^{13}$ cells/μl. Cells were counted before and after concentrating and prior to injection with a hemacytometer. Following the implantation procedure the viability of the cell preparation was assessed by trypan blue exclusion analysis.

Adult female Fischer 344 rats (155–175 grams) were used as host animals. Rats were anesthetized with an intramuscular injection (0.6 ml/kg) of an anesthetic consisting of ketamine (42.8 mg/ml), xylazine (8.6 mg/ml), and acepromazine (1.4 mg/ml) and were placed into a stereotaxic frame. A mid-line incision was made in the scalp, and a burr hole was made with a 0.9 mm drill bit 1.8 mm to the right and 2.5 mm anterior to the bregma. Using a 10 μl syringe fitted with a 26 gauge needle and connected to the manipulating arm of the stereotactic frame, $1 \times 10^4$ 9L glioma cells suspended in 5 μl of HBSS were injected in 0.2 μl increments over 5 minutes into the right caudate nucleus at a depth of 4.5 mm from the dura. The needle was left in place for 3 minutes and then withdrawn slowly over another 3 minutes. The burr hole was closed with bone wax and the scalp wound was closed with clips. Tumors were 1.65±0.094 $mm^2$ (n=4) in diameter 9 days after tumor cell injection and, if left untreated, killed the hosts at a mean time of 20 days after implantation.

Adenoviral Transduction of Experimental Tumors.

Eight days after 9L tumor cell injection either ADV-tk or ADV-βgal was injected into the tumors using the same coordinates that were used for tumor implantation. Viral particles ($1.2 \times 10^9$) in 6 μl of 10 mM Tris-HCl, pH 7.4, 10% glycerol and 1 mM $MgCl_2$ were injected at 6 sites within the tumor bed. Starting at a depth of 5.5 mm below the dural surface, 1 μl of virus was injected and the needle raised 0.5 mm where -another 1 μl was injected. This was repeated until a total of six 1 μl injections were made through the core of the tumor. Virus was injected over 5 minutes at each position and then the needle was withdrawn slowly over 5 minutes. Carbon particles (<30 μm) were placed on the shaft of the injection needle to mark the injection site. The wound was closed with clips.

Ganciclovir Treatment of Experimental Tumors.

To demonstrate the effectiveness of ADV-tk and ganciclovir treatment on experimental 9L tumors, 3 treatment groups were established: 1) ADV-tk plus 100 mg/kg ganciclovir (n=6); 2) ADV-βgal plus 100 mg/kg ganciclovir (n=4); 3) ADV-tk plus saline (n=7). Treatment began 12 hours after viral injection. The animals received intraperitoneal injections of ganciclovir or of normal saline twice a day for 6 consecutive days. Twenty days after tumor cell injection or at death, the animals were perfused with fixative, the brains sectioned and stained, and the tumor size morphometrically determined.

The effect of ganciclovir dosage on the effectiveness of ADV-tk treatment was determined by establishing 7 experimental groups (n=4 for each group) that were implanted with 9L cells, treated with $1.2 \times 10^9$ ADV-tk and then treated with ganciclovir at doses of 0, 10, 20, 50, 80, 100 and 150 mg/kg twice daily for 6 days. Twenty days after tumor induction the animals were perfused with fixative, the brains sectioned and stained, and the tumor size measured.

To show the effect of ADV-tk and ganciclovir treatment on long-term survival, 17 tumor-bearing animals were treated with ADV-tk and ganciclovir (50 mg/kg) and 7 animals were treated with ADV-βgal and ganciclovir (50 mg/kg). The animals were monitored daily and, if they exhibited signs of morbidity or if they died, their brains were removed for histological analysis.

Histological Analysis.

Animals were anesthetized and fixed by cardiac perfusion with 100 ml of 10 mM phosphate buffered saline, pH 7.4 (PBS) containing heparin (10 units/ml) followed by 200 ml of 4% paraformaldehyde in PBS. Brains were removed, placed in 4% paraformaldehyde in PBS for 24 hours, then cryoprotected in 21% sucrose in PBS for 24–48 hours at 40° C., mounted in OCT, frozen and sectioned on a cryostat. Sections were stained with hematoxylin and eosin or prepared for immunocytochemical analysis, The maximal tumor cross-sectional area was measured using Bioscan Optimas software. Mean tumor values were compared using ANOVA statistical analysis. Immunocytochemical staining was performed using ED1 anti-macrophage antibody (Dijkstra et al., 1985; Polman at al., 1986) diluted 1 to 500 on 40 μm sections.

Results

Effect of ADV Gene Therapy on Experimental Gliomas.

When the tumors were treated with ADV-βgal and ganciclovir (100 mg/kg) or with ADV-tk and saline large tumors were present in all brains 20 days after tumor cell injection. The tumors were characterized by hypercellularity, nuclear pleomorphism, and mitoses without inflammatory cell infiltration. The tumors were generally well circumscribed and caused compression of adjacent brain tissue. However, focal peri-vascular glioma infiltration into adjacent brain was seen. In contrast, no tumor cells were seen in the brains of animals that received ADV-tk and ganciclovir (100 mg/kg) treatment. Instead, macrophages, lymphocytes, neutrophils, necrosis and hemorrhage were apparent in the tumor injection area. Although the ipsilateral intraventricular ependymal cell lining appeared damaged in specimens, no necrosis, loss of neurons, demyelination, or inflammatory response was observed beyond the tumors or injection sites.

Dose-Response Effects of Ganciclovir Treatment.

Figure 13:
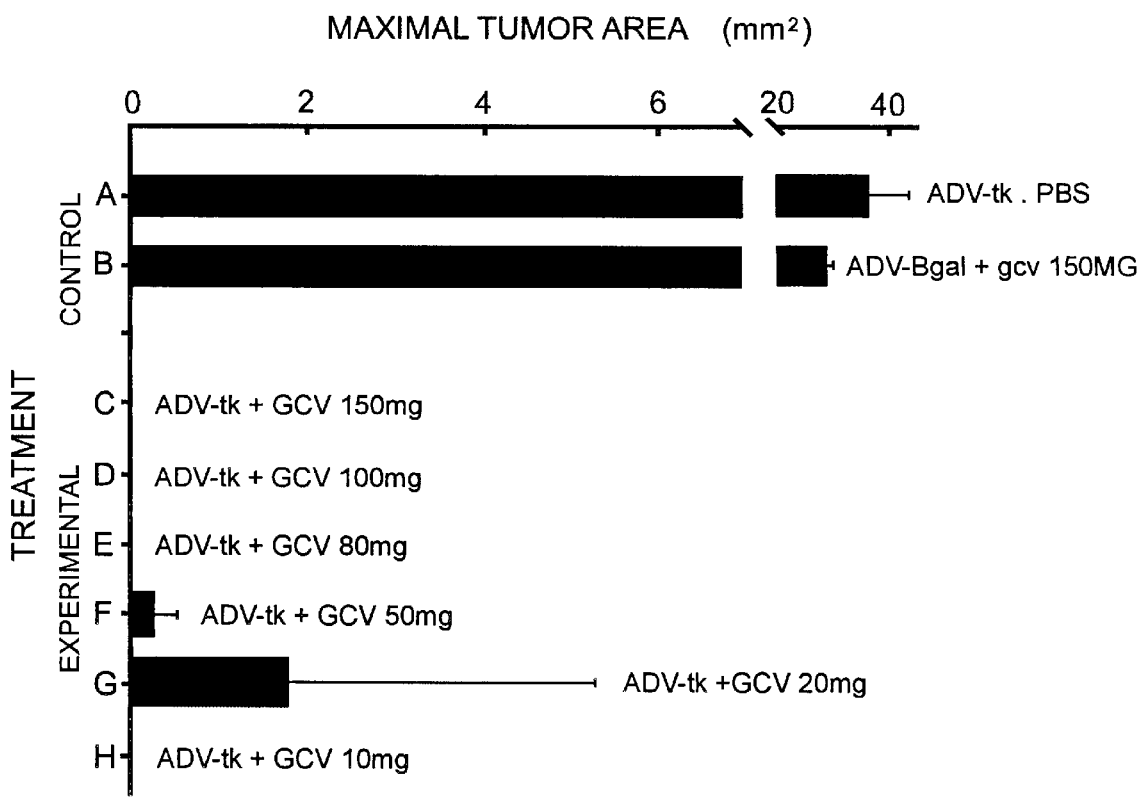
FIG. 13 shows the effect of ganciclovir dose on brain tumor size after adenovirus-mediated gene therapy. Small residual tumors were noted in some brains of ADV/tk treated rats that received less than 80 mg/kg ganciclovir. Error bars=S.D. Treatments, mean tumor areas ±S.D., and sample sizes are: A ADV-tk+PBS, 36.89±6.73 mm$^2$ (n=3); B ADV-βgal+150 mg/kg ganciclovir, 28.75±0.55 mm$^2$ (n=4); C ADV-tk+150 mg/kg ganciclovir, −0 mm$^2$ (n=2); D ADV-tk+100 mg/kg ganciclovir, 0 mm$^2$ (n=4); E ADV-tk+80 mg/kg ganciclovir, 0 mm$^2$ (n=2); F ADV-tk+50 mg/kg ganciclovir, 0.25±0.29 mm$^2$ (n=4); G ADV-tk+20 mg/kg ganciclovir, 1.79±3.52 mm$^2$ (n=4); H ADV-tk+10 mg/kg ganciclovir, 0.01±0.004 mm$^2$ (n=4).

Morphometric analysis of tumor size in animals treated with different doses of ganciclovir showed that even at low (10 mg/kg) doses of ganciclovir the ADV-tk plus ganciclovir treatments had significant effects (P<0.005) on tumor size (FIG. 13). Large tumors were present in animals treated with ADV-tk and saline and in animals treated with ADV-βgal and ganciclovir whereas animals that were treated with ADV-tk and ganciclovir at doses of 80 to 150 mg/kg had no residual tumors. Animals treated with ganciclovir at doses of less than 80 mg/kg had small residual tumors. A significant reduction (P<0.005) in tumor size was present in animals treated with ADV-βgal and 150 mg/kg ganciclovir compared to animals treated with ADV-tk and saline. This suggests that ganciclovir itself may exhibit cytotoxicity or inhibitory effects on tumor growth independent of thymidine kinase activity.

Survival Studies.

Figure 14:
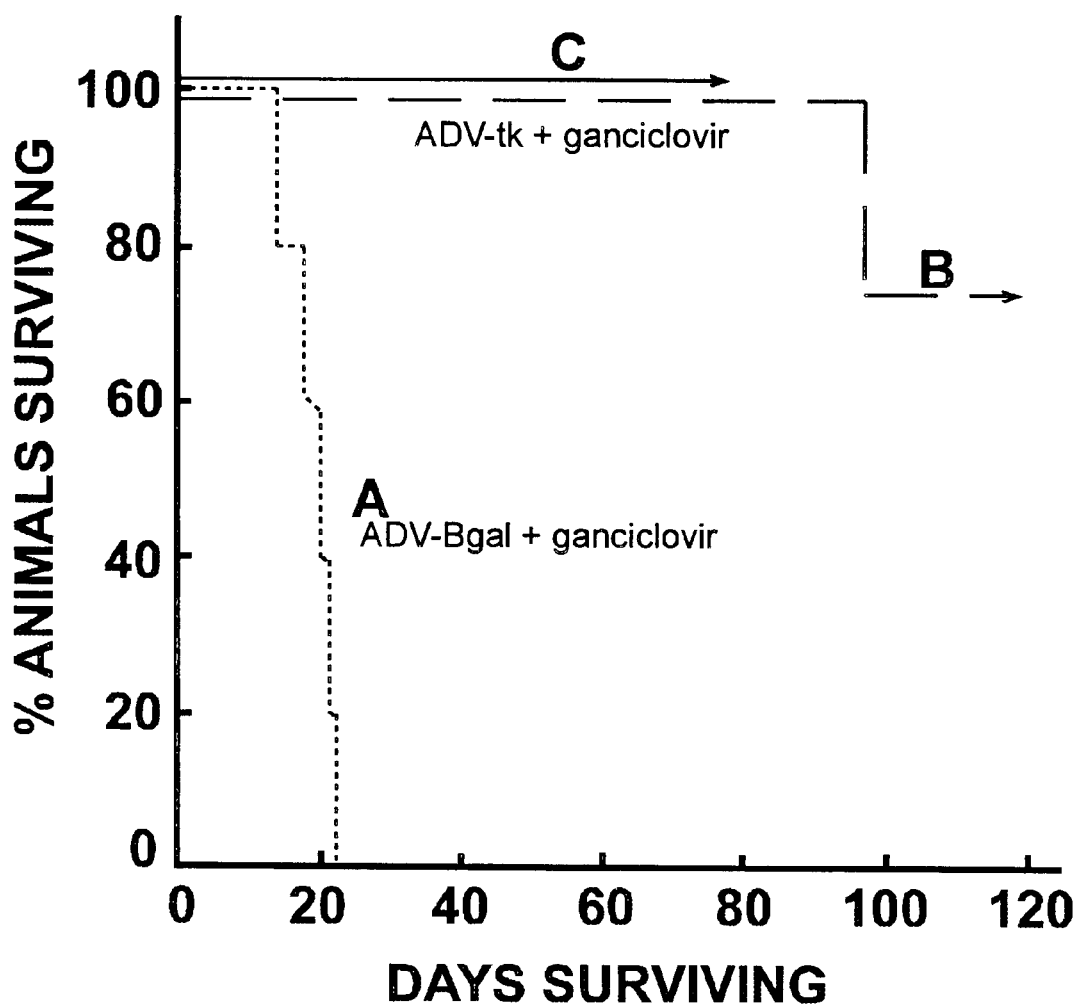
FIG. 14 illustrates the results of a survival study of animals treated with either ADV-βgal or ADV-tk and then 50 mg/kg of ganciclovir twice daily for 6 days. A: those animals treated with ADV-βgal plus ganciclovir died within 22 days (—; n=7); B: animals in first group treated with ADV-tk plus ganciclovir remain alive after 120 days except for one animal that died after 98 days from an unknown cause (. . . ; n=4); C: animals in the second group treated with ADV-tk plus ganciclovir remain alive after 80 days (————; n=5).

Long-term survival of animals treated with ADV-βgal or ADV-tk and 50 mg/kg ganciclovir was measured in two experimental groups and in one control group (FIG. 14). All control animals (n=5) that were treated with ADV-βgal and ganciclovir died within days after tumor injection and had large intracranial tumors upon necropsy. Three of the four animals in the first experimental group that was treated with ADV-tk and ganciclovir (50 mg/kg) survived more than 120 days. One animal died at 98 days. No tumor was present in the brain of this animal and no other cause of death was apparent at necropsy. The second experimental group consisted of five animals, all treated with ADV-tk and ganciclovir (50 mg/kg). All of these animals have now survived for 80 days.

These experiments demonstrate that the transduction of experimental gliomas using a recombinant adenoviral vector carrying HSV-tk confers sensitivity to the cytotoxic drug ganciclovir. Adenoviral vectors infect both dividing and non-dividing cells, and multiple virions can infect a cell, which increases the number of copies of recombinant genes expressed per cell. In this study, no tumors were present in animals treated with ADV-tk and ganciclovir at doses of 80, 100 and 150 mg/kg at 20 days after tumor injection treatment whereas large tumors were present in control animals treated with ADV-tk and saline or ADV-βgal and ganciclovir. At ganciclovir doses of 50 mg/kg and less small residual tumors were observed in some animals at 20 days after 9L cell injection. Despite the presence of residual tumors in animals treated with ADV-tk and 50 mg/kg ganciclovir who were killed for histological study at 20 days after implantation, in survival experiments animals treated using the same protocol have survived as long as 120 days. Because of the rapid in vivo growth of implanted 9L gliosarcoma cells it is doubtful that any residual tumor cells exist in the long-term survivors, or if they do exist their biological behavior must be modified.

EXAMPLE 4

Adenovirus-mediated gene therapy for human head and neck squamous cell cancer in a nude mouse model.

Adenovirus-mediated transfer of the herpes thymidine kinase gene followed by ganciclovir administration was used to treat human head and neck squamous cell cancer implanted into the floor of the mouth of nude mice. Tumors were generated by transcutaneous needle injection of $6 \times 10^6$ cancer cells, and after 14 days, $10^{10}$ particles of a replication defective recombinant adenovirus containing the herpes simplex virus thymidine kinase gene (ADV/RSV.TK) were injected directly into the tumors. The mice were subsequently treated with GCV for 6 consecutive days and then sacrificed at 21 days post tumor implantation. Clinical response to the treatment was assessed by computer. Imaged morphometric analysis of cross sectional area of non-necrotic tumor and mitotic-activity with the calculation of a tumor index. The median tumor index value of the complete treatment group was 280 to 2400 fold smaller than controls which did not receive the therapeutic gene (p<0.001–0.016), and three-quarters of the treatment group had tumor index values that were indicative of near total tumor regression. These results demonstrate that clinically effective in vivo treatment of human squamous cell cancer was achieved using adenovirus-mediated gene therapy.

Adenoviral Constructs.

ADV-tk vector was prepared by inserting HSV-tk into the plasmid which contained the Rous sarcoma virus long-terminal-repeat promoter (RSV-LTR) to generate pADL.1/RSV-tk (Chen et al., 1994). Recombinant adenovirus was produced by co-transfecting 293 cells with pADL.1/RSV-tk and a plasmid, pJM17, containing the adenovirus genome. The 293 cells are transformed human kidney cells the E1 region of the adenovirus genome. When 293 cells were co-transfected with pADL.1/RSV-tk and pJM17, replication-defective adenovirus was by homologous recombination (Graham and Prevec, 1991). Virus titer was determined by optical absorbance at 260 nm. A replication-deficient adenovirus vector carrying the E. coli β-galactosidase gene under control of the RSV-LTR (ADV-βgal) was used as a control vector.

In vitro experiments.

$5 \times 10^5$ HLAC-79 cells were plated on 1.5 cm diameter tissue culture plates in Eagle's MEM media containing 10% fetal calf serum with essential amino acids and vitamins. At approximately 50% cell confluence, the recombinant adenoviral vector containing the bacterial β-galactosidase gene (ADV/RSV-β-gal) (Stratford-Perricaudel, et al., J. Clin. Invest. (1992)) was added at various multiplicities of infection. The transduced cells were then stained with X-gal 24 hours after transduction. Under identical conditions, separate cell culture experiments were performed using the ADV/RSV-TK vector followed by either PBS or GCV treatment at a concentration of 10 ug/ml. Sixty-eight hours later, the surviving cells were counted and compared to the PBS control plates.

In vivo experiments.

All animal experiments were performed on athymic nude (nu/nu)—mice (Harlan Sprague Dawley) using sterile technique under a laminar flow hood. Nude mice 6–10 weeks old were anesthetized by intraperitoneal injection of 0.5 ml avertin at a concentration of 20 mg/ml. Using a 100 ul syringe and 26 gauge needle, a 50 ul solution containing $6 \times 10^6$ human HIAC-79 squamous cells in Hank's buffered saline was injected into the floor of the mouth of nude mice. The cell suspension was slowly injected at the depth of the mylohyoid muscle and then the needle was removed with no apparent leakage. The animals were then maintained in standard housing conditions for 14 days.

For the adenovirus injection, the nude mice were anesthetized as before and the neck skin was incised with scissors. The tumors were exposed by careful surgical dissection, and size was measured in three dimensions using calipers. A microliter syringe fitted with a 25 gauge needle was then used to directly inject a 75 ul solution containing $1 \times 10^{10}$ adenoviral particles of either ADV/RSV-TK or ADV/RSV-βgal. Another control group received only 75 ul of phosphate buffered saline (PBS). The actual adenovirus or PBS delivery was performed with four separate needle passes, two parallel to the long axis of the tumor and two perpendicular to this axis. Neck incisions were closed with 4-0 silk (Ethicon). Eighteen hours after virus injections, the mice were begun on intraperitoneal ganciclovir treatments at 100 mg/kg or PBS at the same volume for six days. The treatment mice showed no change in eating or other behavior habits during the course of the ganciclovir treatment.

The mice were sacrificed 21 days after original tumor implantation and the lesions were carefully excised to include only the necrotic or residual tumor mass. The tumor masses were measured with calipers immediately after excision and then repeat measurements were made by a second independent examiner prior to embedding for -histologic evaluation. For X-gal studies, excised tumor was embedded in O.C.T. and snap frozen over dry ice. It was stored at −80° C. until preparation of frozen sections which were stained with X-gal (Ponder et al., PNAS (1988)). For all other histologic studies, tissue was fixed in 10% buffered formalin, embedded in paraffin, serial 3 micron sections cut, and stained with hematoxylin and eosin. Histologic sections were examined by a single individual (M.R.S.) who was blinded to the particular treatments of each animal. Assessment of tumor grade, circumscription, necrosis, fibrosis, inflammatory response, and mitotic counts were done using standard microscopic equipment. Quantitative morphometric measurements of maximum tumor cross-sectional area, per cent tumor necrosis per cross-sectional area, and mitotic figures per 10 high power fields were performed using a computer-assisted image. analyzer. The system includes a Nikon Microphot-FXA microscope, Ikegami 370M high resolution color camera, Sony Triniton high resolution color video monitor, and a Compudyne 486 computer with Bio-scan optimas software (Edmonds, Wash.).

Results

Efficiency of adenoviral transduction of HlaC-79 cells in vitro.

Figure 15:
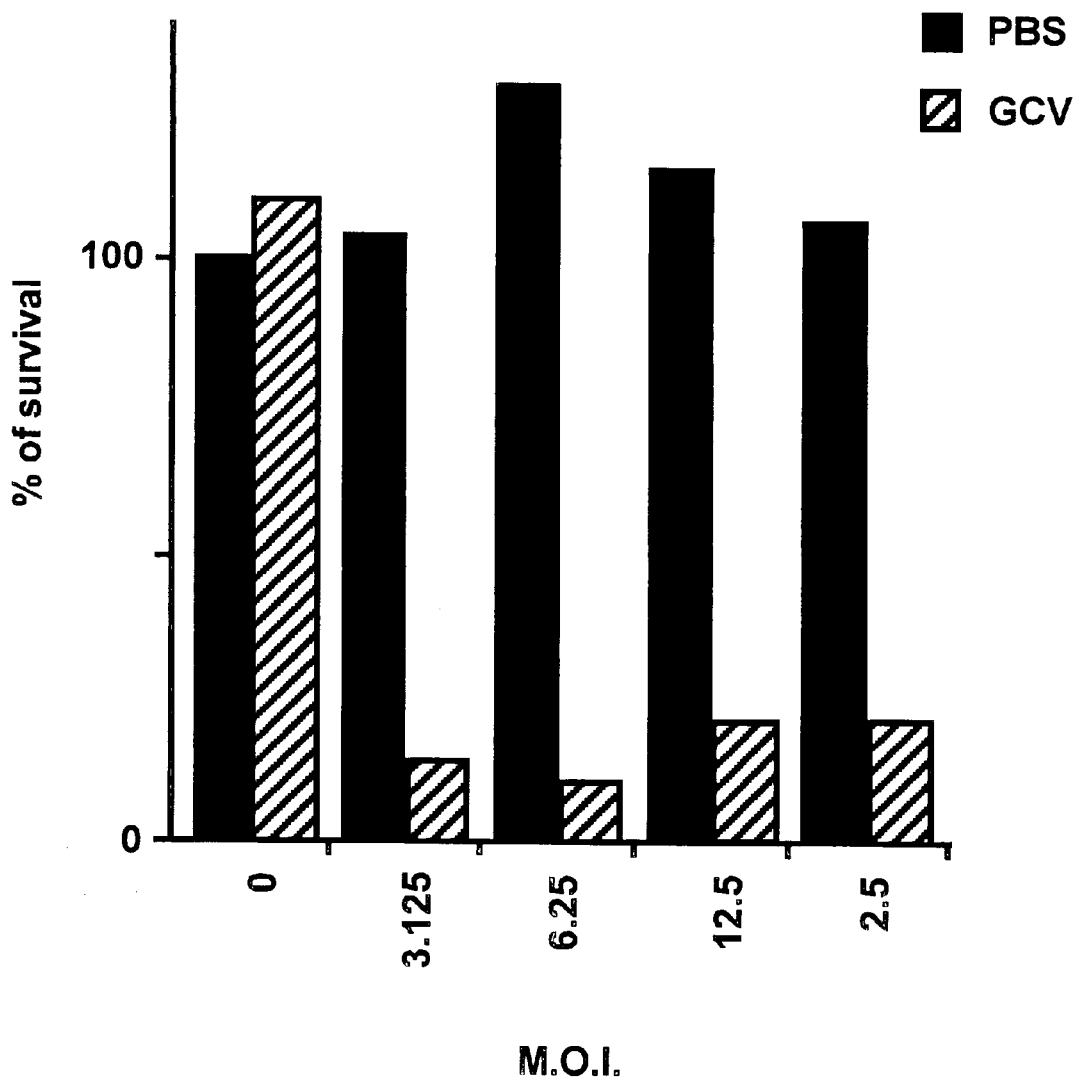
FIG. 15 shows ADV/RSV-TK transduction of HLaC-79 human squamous cancer cells in vitro followed by treatment of either GCV 10 ug/ml (solid bars) or PBS (striped bars). Call survival was assessed 68 hours after transduction in both GCV treatment and PBS control groups. Treatment with GCV resulted in 85–90x cancer cell killing at very low M.O.I. Nontransduced controls (M.O.1=0) and PBS controls demonstrated no toxicity up to an M.O.I. of 25.

For the ADV/RSV β-gal experiments, 85% of the human squamous cancer cells were transduced at a M.O.I. of 8 as demonstrated by positive blue X-gal staining, and 100% of cells were transduced at an M.O.I of 16. There was no apparent toxicity at this adenovirus concentration and the cancer cells showed no morphologic changes compared to controls. For the ADV/RSV-TK experiments, transductions were performed using a range of 0 (control) to 50 M.O.I. followed by either PBS or GCV treatment in the media. Effective cancer cell killing in the GCV group was achieved at a very low M.O.I of 3 with no increased killing and no toxicity in the PBS group up to an M.O.I of 25 (FIG. 15). Significant cell death was seen in cultures of squamous carcinoma cells transduced with adenovirus at 50 or higher M.O.I. but not subjected to GCV treatment. These findings indicate that ADV/RSV-TK is an efficient vector system that is effective in killing human squamous cancer cells in vitro in combination with GCV.

Regression of human squamous cell cancers after adenoviral transduction. After original implantation of $6 \times 10^6$ tumor cells, the mice showed slow clinical tumor growth in the floor of mouth with extension into the anterior neck over the following two weeks. There were no signs of cachexia during this period. and all animals appeared healthy at the time of adenovirus injections. One control group of animals was sacrificed at two weeks and histopathological examination revealed a poorly differentiated squamous cell cancer with many mitotic figures and without keratin formation or necrosis. There was also clinical and histopathologic evidence of surrounding soft tissue, muscle, and bony invasion. A second group of control animals eventually developed cachexia and died after 35–45 days.

In the clinical experiment, there were four control groups and one complete treatment group: (1) PBS intratumor injection plus GCV treatment (PBS+ G+); (2) ADV/RSV-β-gal plus PBS (β-gal+ G−); (3) ADV/RSV-β-gal plus GCV (β-gal+ G+); (4) ADV/RSV-TK plus PBS (TK+ G−): and (5) ADV/RSV-TK plus GCV (TK+ G+). The experimental animals showed no signs of cachexia or change in eating habits during the treatment period and all appeared clinically healthy at necropsy. The pre-treatment tumor sizes ranged from 4.36 $mm^2$ in cross sectional area with an average of 13.7 $mm^2$ for all groups and 16.4 $mm^2$ for the TK+ G+ complete treatment group. The wide variations in tumor size are consistent with the original and only report of this cancer model (Dinesman et al., *Otolaryngol Head Neck Surg.*, (1990)).

Figure 16:
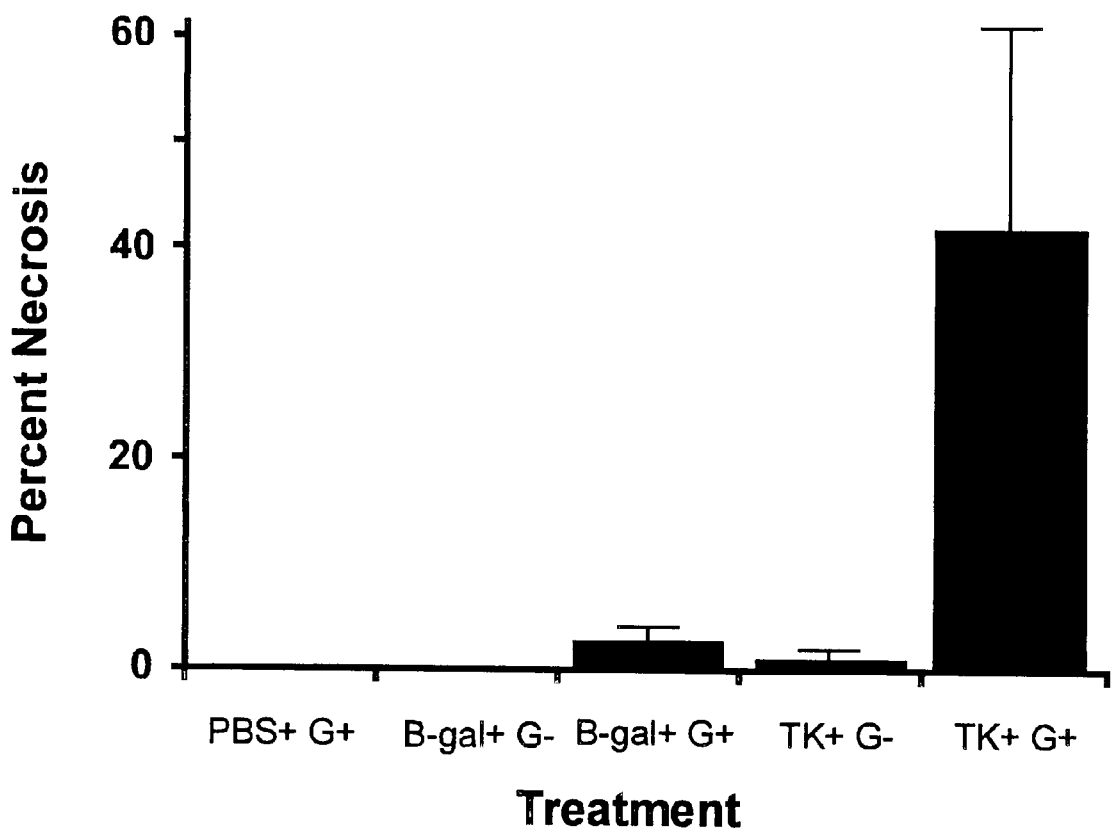
FIG. 16 presents the mean percent necrosis of squamous cell tumors in vivo for each experimental group. A substantial cytotoxic effect (41% necrosis) was seen after adenovirus transduction and ganciclovir treatment (TK+C+) compared to controls (0–2.2% necrosis). Statistical significance per t-Test analysis: p<0.001.

The cytotoxic effects of the treatments were assessed histologically by measuring percent necrosis in the tumor masses using computer assisted image analysis The PBS+ G+ and β-gal+ G− animals showed no tumor necrosis, and the TK+G− and β-gal+ G+ groups showed only focal areas of necrosis ranging from 0.5–5.0% of the mean cross sectional area. The TK+ G+ group, however, showed substantial diffuse necrosis ranging from 17–72% of the tumor mass with a mean value of 41% that was statistically different from the controls using t-Test analysis (p<0.001) (FIG. 16).

X-gal staining of sections of tumor injected with ADV/RSV-Bgal demonstrated positive nuclear staining of 1–10% of tumor cells in a distribution consistent with the regions of needle injection. Small islands of residual tumor could be identified in most of the complete treatment (TK+ G+) animals, however microscopic examination revealed swollen dying tumors or individually necrotic cells in these areas. There was also very low or absent mitotic activity. Three tumor specimens showed marked fibrous obliteration with only small islands of dying carcinoma cells within dense fibrous tissue. Only the two largest tumors in the TK+ G+ group (220 and 324 $mm^3$ at transduction) showed substantial areas of viable tumor cells after treatment.

Figure 17:
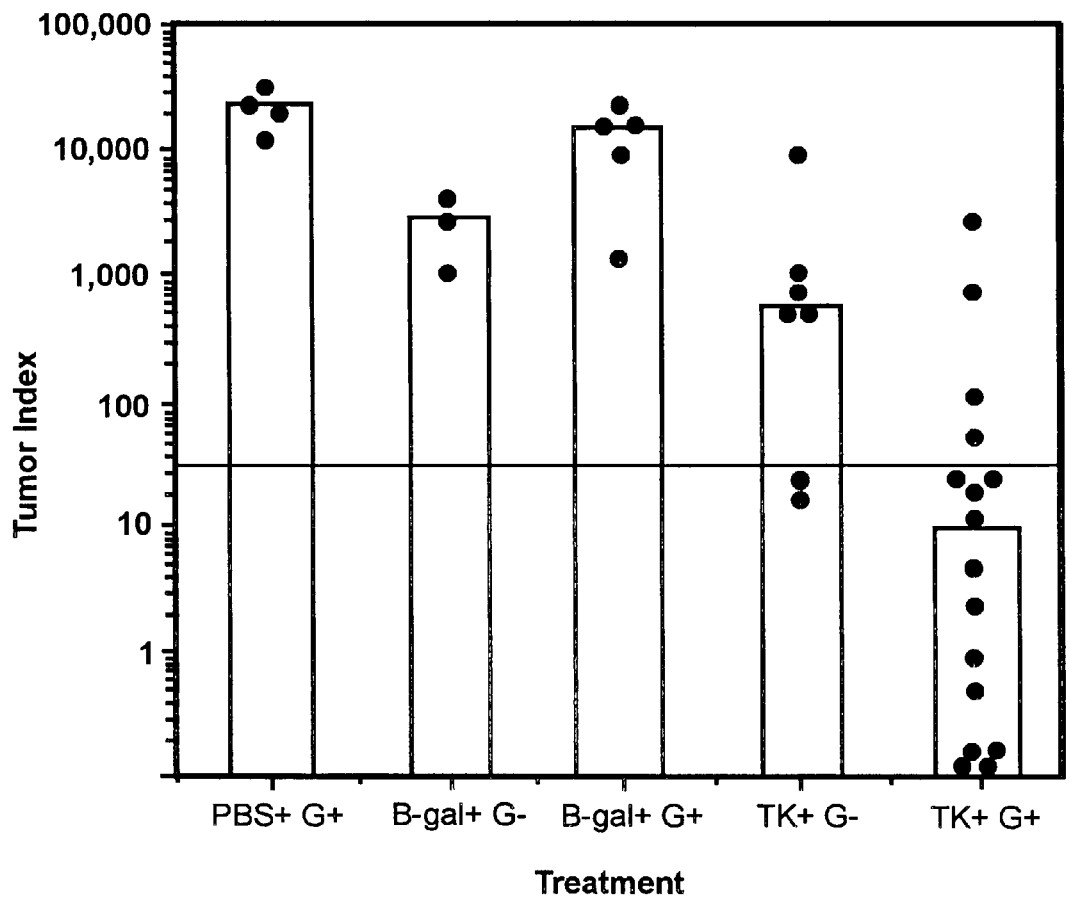
FIG. 17 shows tumor index values (dots) depicting the overall clinical response for each animal in the experimental groups. Data at or below the horizontal line (tumor index of 30 or less) indicate near total tumor regression. Bars show median values for each group. Dramatic clinical response was seen in the complete treatment animals (TK+G+) compared to each control group (p<0.001–0.02 per Mann-Whitney analysis).

In order to objectively analyze these findings, a tumor index value indicating overall clinical response was determined for each group using a modification of the previously described cancer cell index calculation (Caruso et al, PNAS (1990)). The tumor index was based on morphometric measurements of maximum cross-sectional tumor area multiplied by the mitotic activity of non-necrotic tumor mass and change in macroscopic size. The majority of animals in the TK+ G+ group had a tumor index of "30" or less which reflects near total tumor regression with only rare viable tumor cells noted on microscopic analysis (FIG. 17). A value of "0" occurred in four TK+ G+ animals and correlates not only with an absence of mitotic figures but also a lack of characteristic viable tumor cells upon histologic examination. The mean tumor index for the complete treatment group (TK+ G+) was 10–100 fold smaller and the median value was 280–2400 fold smaller than values for the control groups which did not receive the therapeutic TK gene. When compared to the TK group that did not receive ganciclovir (TK+ G−), the TK+ G+ treatment group had mean and median tumor index values which were 6- and 55-fold smaller. Using Mann-Whitney analysis, statistical significance was determined by comparing the TK+ G+ group to each of the controls with values ranging from p<0.001 to p<0.02 (FIG. 16).

Local and systemic effects of adenovirus gene transfer and ganciclovir treatment.

Two of the animals that received ADV/RSV-TK and ganciclovir treatment were chosen at random and samples of local tissue and distant organs were evaluated for any histological abnormalities. Surrounding muscle, soft tissue, and salivary glands in the floor of mouth and neck regions did not show any evidence of necrosis, dying cells, or morphologic changes. Distant organs were also harvested at necropsy and included small intestine, bladder, ovaries, spleen, heart, brain, kidney, lung, and liver. All specimens were normal on gross examination and histological analysis revealed no metastatic tumor, necrosis, fibrosis, or other abnormal morphology. Over all, local and distant tissues appeared normal with no apparent effects of adenovirus or ganciclovir treatment.

These experiments are the first successful demonstration of adenoviral-mediated gene transfer utilized for the treatment of human head and neck squamous cell carcinoma in a nude mouse model. The effectiveness of the treatment scheme is depicted by the very low M.O.I needed for in vitro killing and results of the two therapeutic indices analyzed. This human cancer cell line is highly susceptible to transduction via the adenovirus vector system as dramatic killing occurred at an M.O.I. as low as 3. The susceptibility to adenoviral transduction should prove advantageous by allowing lower concentrations of ADV/RSV-TK to be delivered to tumors while maintaining successful clinical response.

The first therapeutic index is mean tumor necrosis which was high for the ADV/RSV-TK plus GCV group (TK+ G+), indicating a substantial cytotoxic effect of the coupled therapy. Treatment with ganciclovir alone (PBS+ G+) or in conjunction with the g-gal vector (β-gal+ G+) showed no tumor necrosis, and two of the seven tumors injected with the thymidine kinase vector alone (TK+ G−) showed only microscopic regions of focal necrosis. The remaining experimental group, β-gal vector alone (β-gal+ G−), contained microscopic focal necrosis in each tumor which was consistent with the sites of needle injection. Thus, the combination of thymidine kinase gene transfer plus ganciclovir is essential in direct tumor eradication.

The second therapeutic index is based on morphometric analysis and histologic characteristics of the tumors and has been designated the tumor index. The importance of this calculation method for tumor index is that it provides an objective means of assessing any apparent residual tumor as well as the overall treatment outcome, thereby eliminating possible examiner bias in interpreting tumor histology. The majority of animals in the complete treatment group (TK+ G+) had tumor index below "30" indicating near total tumor eradication, and four animals had values of "0". These findings demonstrate a definite therapeutic effect of the thymidine kinase gene transfer and ganciclovir treatment.

There were two high clinical response values in the TK+ G+ treatment group which result from incomplete tumor killing and areas of residual viable cancer. Upon reviewing the pre-treatment gross size, the tumor volumes for these animals were 324 and 220 mm$^3$ compared to an average volume of 95 mm$^3$ for the other tumors in the TK+ G+ group. These findings suggest that a critical tumor volume exists which limits the response of "one time" gene transfer therapy. There were also two low clinical response values in the TK+ G− control group, but on histological review there was no evidence of necrosis, and the tumor contained large numbers of mitotic figures. These low values were a direct result of the very small cross sectional area of the two tumors and could simply be a factor of the known variable cancer growth in this model (Dinesman et al., *Otolaryngol Head Neck Surg.*, (1990)). The possibility of an inhibitory effect on tumor growth from thymidine kinase gene transfer must be considered, however, since the tumor indices of the TK+ G− group were overall smaller than both the PBS and β-gal adenovirus gene transfer control animals (p<0.010–0.016). The β-gal+ G+ and β-gal+ G− control animals also showed no statistical differences in tumor response from the PBS+ G+ control group.

Athymic mice which lack T-cells (CD4+ and CD8+ lymphocytes) were selected in these experiments for the purpose of eliminating the cellular immune response which has been implicated as a major component of tumor regression after viral transduction (Caruso et al., PNAS (1990); Culver et al., *Science* (1992)). Previous studies on retroviral-mediated TK gene transfer into rat glioma tumors in immune-competent animals have shown that infiltration of macrophages and lymphocytes occurs in these tumors (Culver et al, *Science* (1992)). It is believed that this immune reaction enhances general tumor killing after viral transfer. In our experiments, there was no inflammatory or immune cell response in the TK+ G+ treatment group or any of control groups. Therefore, the tumoricidal response directly results from the thymidine kinase gene transfer coupled with ganciclovir administration.

The findings in our studies do support the concept of a contribution from what has been called "the bystander effect". In both murine and human sarcoma tumor models, the transfer of a toxic metabolite of ganciclovir, presumably a phosphorylated form, via gap junctions or endocytosis of apoptotic vesicles from virally transduced dying tumor cells to nearby nontransduced cells has resulted in killing of these "bystander" cells. In our experiments with human squamous cell cancer in vivo, ADV/RSV-β-gal delivery resulted in only a 1–10% transduction as detected by X-gal staining, whereas the same quantity of virus injection with ADV/RSV-TK showed diffuse tumor killing and necrosis in the experimental group. Furthermore, the localized β-gal staining indicates that the adenovirus does not readily diffuse throughout the solid tumor to affect cancer cells distant to the site of delivery. It should also be noted that in vitro, similar transduction efficiencies occurred at low multiplicity of infection for both the β-gal and TK adenovirus. The extent of tumor killing in these large floor of mouth squamous cancers after adenoviral transduction may occur in conjunction with some other component such as the bystander effect.

Although the ADV/RSV-TK was injected directly into the tumors, some leakage did occur onto surrounding muscle, salivary gland, and subcutaneous tissues. Microscopically, there was no necrosis or change in morphology of these surrounding normal tissues. The effects of the adenoviral-TK transduction and GCV administration are thus limited to the actively dividing cancer cells. There was also no evidence of systemic damage from the treatment regimen as gross and microscopic inspection of distant organs including small intestine, bladder, ovaries, spleen, heart, brain kidney, lung, and liver revealed no injury.

These experiments demonstrate that clinically effective in vivo treatment of human squamous cell cancer in an animal model can be achieved using adenovirus-mediated gene therapy.

EXAMPLE 5

Combination gene therapy for liver metastasis of colon carcinoma in vivo.

The efficacy of combination therapy with a suicide gene and a cytokine gene to treat metastatic colon carcinoma in the liver was investigated. Tumors in the liver were generated by intrahepatic injection of a colon carcinoma cell line (MGA 26) in syngeneic BALB mice. Recombinant adenoviral vectors containing various control and therapeutic genes were injected directly into the solid tumors, followed by treatment with ganciclovir. While the tumors continued to grow in all animals treated with a control vector or a mouse interleukin-2 vector, those treated with a Herpes Simplex Virus/thymidine kinase vector, with or without the co-administration of the mouse interleukin-2 vector, exhibited dramatic necrosis and regression. However, only animals treated with both vectors developed an effective systemic anti-tumoral immunity against challenges of tumorigenic doses of parental tumor cells inoculated at distant sites. The anti-tumoral immunity was associated with the presence of MCA26 tumor specific cytolytic CD8+ T-lymphocytes. The results suggest that combination suicide and cytokine gene therapy in vivo is a powerful approach for treatment of metastatic colon carcinoma in the liver.

Construction of Recombinant Adenoviral Vectors.

Construction of a replication-defective adenoviral vector containing the Herpes Simplex Virus Thymidine Kinase gene (ADV/RSV-tk) has been reported previously (Chen, et al., PNAS (1994)). A replication-defective adenoviral vector containing the mouse interleukin 2 cDNA (ADV/RSV-mIL2) was similarly constructed. The peptide coding region of a mouse interleukin 2 (mIL-2) cDNA was inserted into an expression cassette consisting of the RSV-LTR promoter and the polyadenylation region of the bovine growth hormone gene in an E1A-adenoviral vector backbone (Fang et al., Cancer Res. (1994)). The construct was co-transfected into 293 cells with pJM17 DNA, which contains the complimenting adenoviral genome. The recombinant adenovirus was isolated by plaque purification followed by double cesium chloride gradient centrifugation. The viral titer (pfu/ml) was determined by plaque assay.

Establishment and Treatment of Hepatic Metastasis Model of Colon Carcinoma.

Metastatic colon carcinoma was induced in the liver by intrahepatic implantation of MCA-26 cells, which is a chemically induced, poorly differentiated colon carcinoma cell line derived from BALB/c mice (Corbett et al., Cancer Res. (1975)). The liver was exposed by abdominal incision and $3 \times 10^5$ MCA-26 cells were injected at one site at the tip of the left lateral lobe of syngeneic mice. At day 7, the liver was exposed by abdominal incision and the tumor sizes were measured. Various titers of recombinant adenoviral vectors were injected directly into the hepatic tumors in 70 μl of 10 mM Tris-HCl, pH 7.4, 1 mM $MgCl_2$, 10% glycerol and 20 μg/ml of polybrene. Twelve hours after viral injection, the animals were treated intraperitoneally with ganciclovir (GCV) at 35 mg/kg twice daily for 6 consecutive days.

Histopathological and Morphometric Analysis of Residual Tumors.

After various gene therapy treatments, computerized morphometric analysis of the largest cross-sectional areas of the residual tumors was performed. The point counting method using a computer assisted digitizing system with Bioquant software was chosen for morphometric analyses as viable tumor cells were not always contiguous. Briefly, more than 1,600 predetermined points in the region of the tumor were counted. The proportion of viable tumor cells in the nodule equalled the sum of the points of viable tumor cells divided by total number of points. The functional area of viable tumor cells among the groups was compared by ANOVA.

Distant Site Challenge in Treated Animals with Parental Tumor Cells.

One day after completion of GCV treatment, which was 2 weeks after MCA-26 tumor cell implantation in the liver, animals in all treatment groups were challenged with tumorigenic doses of the parental tumor cells (MCA-26) as well as a heterologous but syngeneic breast tumor cell line (MOD). $1 \times 10^5$ MCA-26 cells were injected subcutaneously at a single site on the right flank of the animals and $2 \times 10^6$ MOD cells were injected subcutaneously on the contralateral site. Visible subcutaneous tumors of similar sizes developed in the normal recipient animals after one week, and the presence of subcutaneous tumors in animals after various gene therapy treatments was observed for 4 weeks.

Cytotoxic T-Lymphocyte (CTh) Assay.

The CTL assay was performed according to published procedures (Coligan et al., Current Protocols in Immunology (1991)). Viable splenocytes were isolated from various animal treatment groups at 3 days after completion of GCV treatment, which was 10 days after adenoviral vector injection. In vitro stimulation was performed in 24 well plates with $6 \times 10^6$ splenocytes and $5 \times 10^5$ 15,000 RAD-irradiated MCA-26 cells per well, plus 20 U/ml recombinant murine IL-2. $^{51}$Cr release assays were performed by mixing various numbers of stimulated splenocytes harvested after 5 days of culture (effector cells) with 5000 $^{51}$Cr-labelled MCA-26 cells (target cells) in 96-well U-bottom plates. After 4 hours at 37° C. 100 μl of medium was removed from each well and counted in a gamma counter. Percent cell lysis is defined as $[(cpm_{exp} - cpm_{min})/(cpm_{max} - cpm_{min})] \times 100$, where $cpm_{max}$ represents total counts released by NP40-lysed target cells and $cpm_{min}$ represents background counts spontaneously released by the target cells. Data represent mean specific cpm of triplicate cultures, with SEM less than 7% in all assays.

Results

Functional Characterization of Recombinant Adenoviral Vectors.

Figure 18:
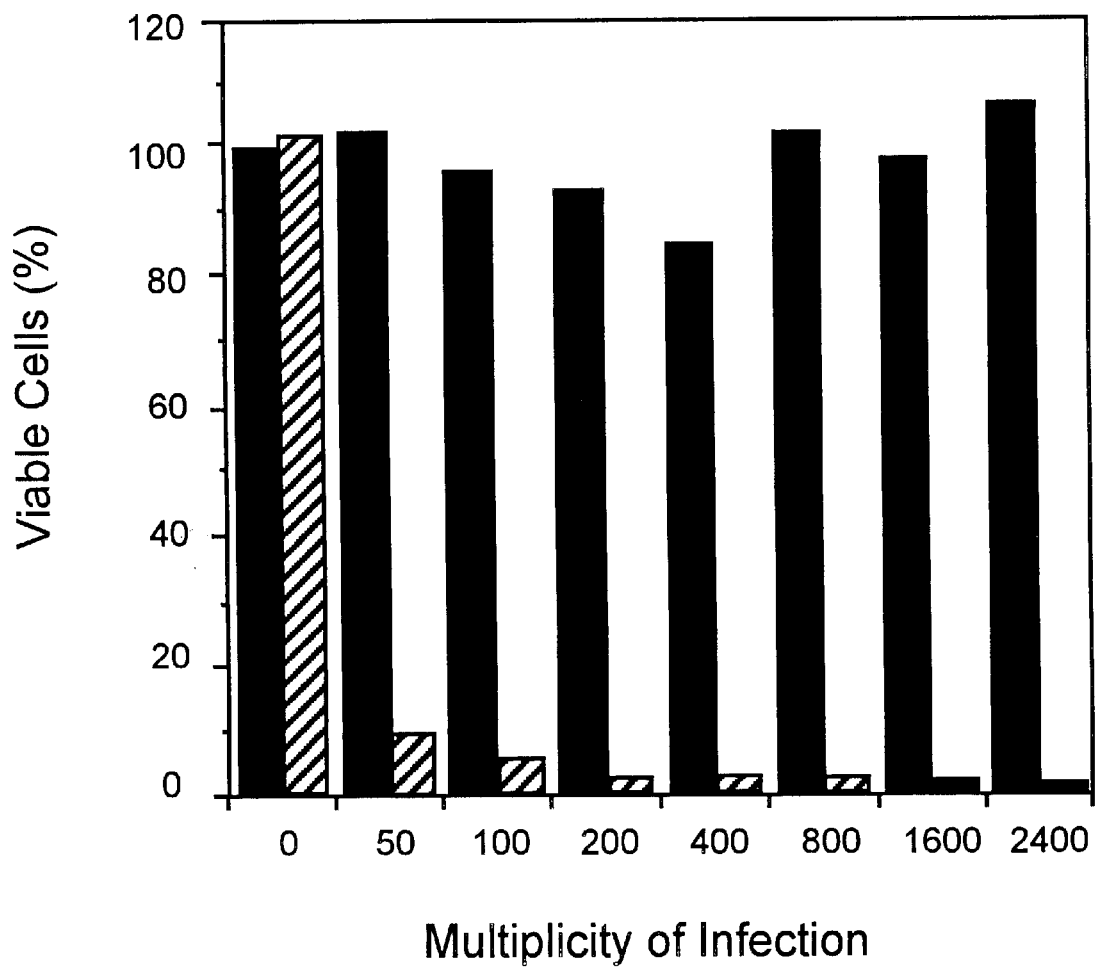
FIG. 18 shows the functional characterization of the recombinant adenoviral vectors: GCV susceptibility of ADV/RSV-tk transduced MCA-26 colon tumor cell lines. MCA-26' cells were transduced with ADV/RSV-tk at various multiplicities of infection, followed by either PBS or 10 ug/ml GCV treatment 12 hours later. After 3 days, the viable cells were determined by trypan blue staining.
Figure 19:
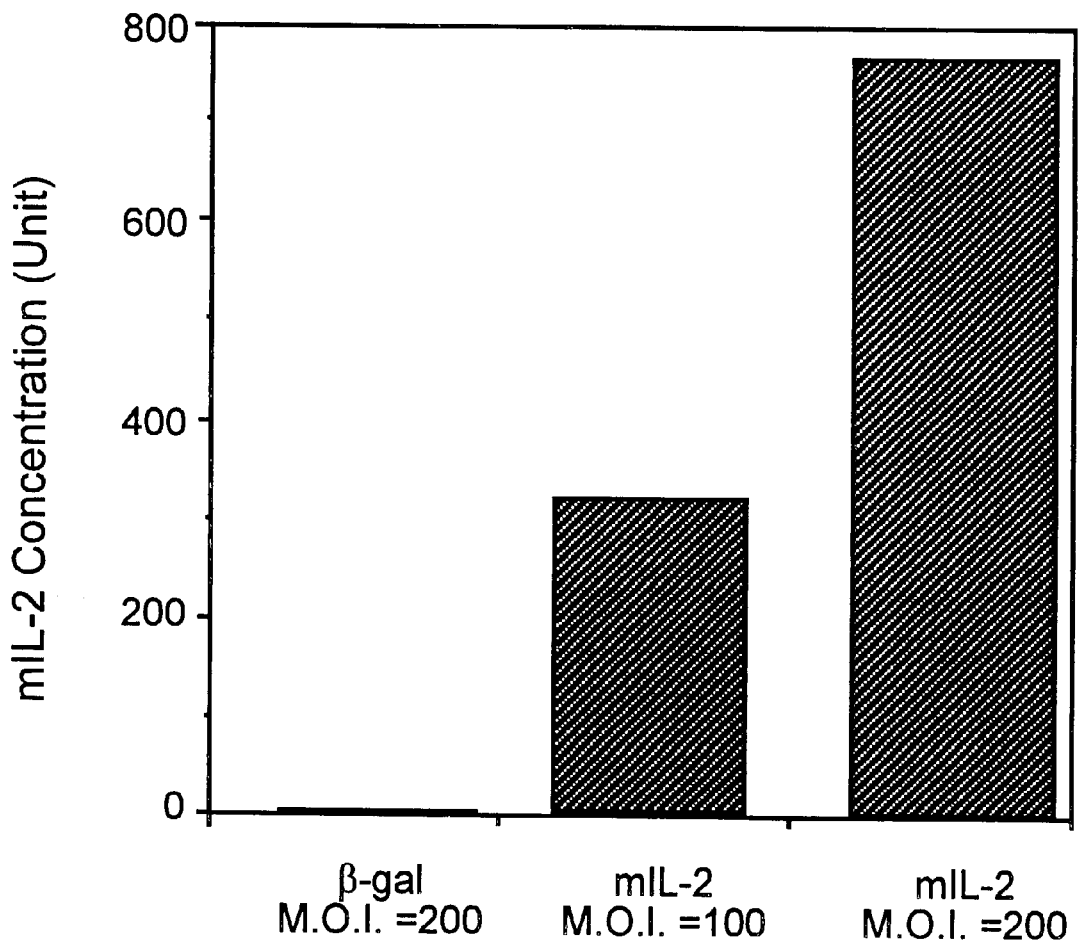
FIG. 19 shows the results of a mouse IL2 bioassay of conditioned media from B16 cells transduced with ADV/RSV-mIL2. The conditioned media were added to a mouse T-cell line CTLL-2 and cultured for 20 hrs. $^3$H:thymidine was added for another 4 hrs and the cells were collected using a PHD cell harvester. Incorporated $^3$H-thymidine was determined by liquid scintillation counting and mean cpm of triplicate cultures is shown.

To determine whether introduction of the HSV-tk gene would render the MCA 26 colon tumor cells susceptible to killing by GCV, the replication-defective recombinant adenoviral vector ADV/RSV-tk was used to transduce the colon carcinoma cell line in vitro (FIG. 18). After transduction with the recombinant vector and subsequent treatment with PBS, the cells were completely viable even at a multiplicity of infection (M.O.I.) of 12,000. After subsequent GCV treatment, however, only about 10% of the cells were viable at an MOI of 250 and there were few surviving cells at an MOI of 1,000. The functionality of the replication defective mIL-2 adenoviral vector (ADV/RSV-mIL2) was illustrated by transduction of mouse B16 cells in vitro, followed by demonstration of mIL2 activity in the conditioned media using a T-cell proliferation assay (Coligan et al., Current Protocols in Immunology (1991)). A high level of mIL-2 activity was present in the conditioned media of cells after transduction with mIL-2 adenoviral vector at an MOI of 500 and 1,000, but no mIL-2 activity was detected in cells transduced with a control adenoviral vector (FIG. 19).

Regression of hepatic MCA 26 tumors in syngeneic animals after combination gene therapy in vivo.

An animal model for metastatic colon carcinoma in the liver was established by intrahepatic implantation of $3 \times 10^5$ MCA-26 cells. After 6 days, $5 \times 7 mm^2$ tumors were present in the liver of 60–70% of the animals. This was the tumor size selected for all subsequent gene therapy experiments. BALB/c mice with hepatic colon carcinoma were divided into five treatment groups: A: ADV/RSV-βgal; B: ADV/RSV-m1L2; C: ADV/RSV-βgal + ADV/RSV-mIL2; D: ADV/RSV-tk and E: ADV/RSV-tk+ ADV/RSV-mIL2. The residual solid tumors in various animal treatment groups were measured and examined histopathologically. The animals that were treated with the β-gal vector had large nodules of actively growing undifferentiated carcinoma with rare and small foci of spontaneous necrosis and many mitoses. There was compression of the adjacent liver and insignificant inflammation. The animals that were treated with the m1L2 vector displayed limited subscapular necrosis, but had large nodules composed of mostly viable tumor cells with mitotic activity equal to the βgal vector treated mice. There was a moderate inflammatory infiltrate of lymphocytes, macrophages and eosinophils at the border of the tumor. Interestingly, animals treated with a combination of βgal and m1L2 vectors had more tumor necrosis with infiltration of inflammatory cells but viable tumor cells remained. The tk vector treatment group had abundant tumor necrosis, but actively replicating neoplastic cells still remained plentiful. All animals that were treated with the tk+mIL2 vectors exhibited massive tumor necrosis surrounded by inflammatory cells. In some livers, no viable malignancy remained. The large zone of necrosis included a mixture of completely destroyed tumor, hemorrhage and ischemic liver damage. There were numerous macrophages, lymphocytes and granulocytes throughout. Seven of the 10 animals in the tk+mIL2 combination treatment group had few residual tumor cells present and the remaining 3 animals appeared to be tumor-free.

Figure 20:
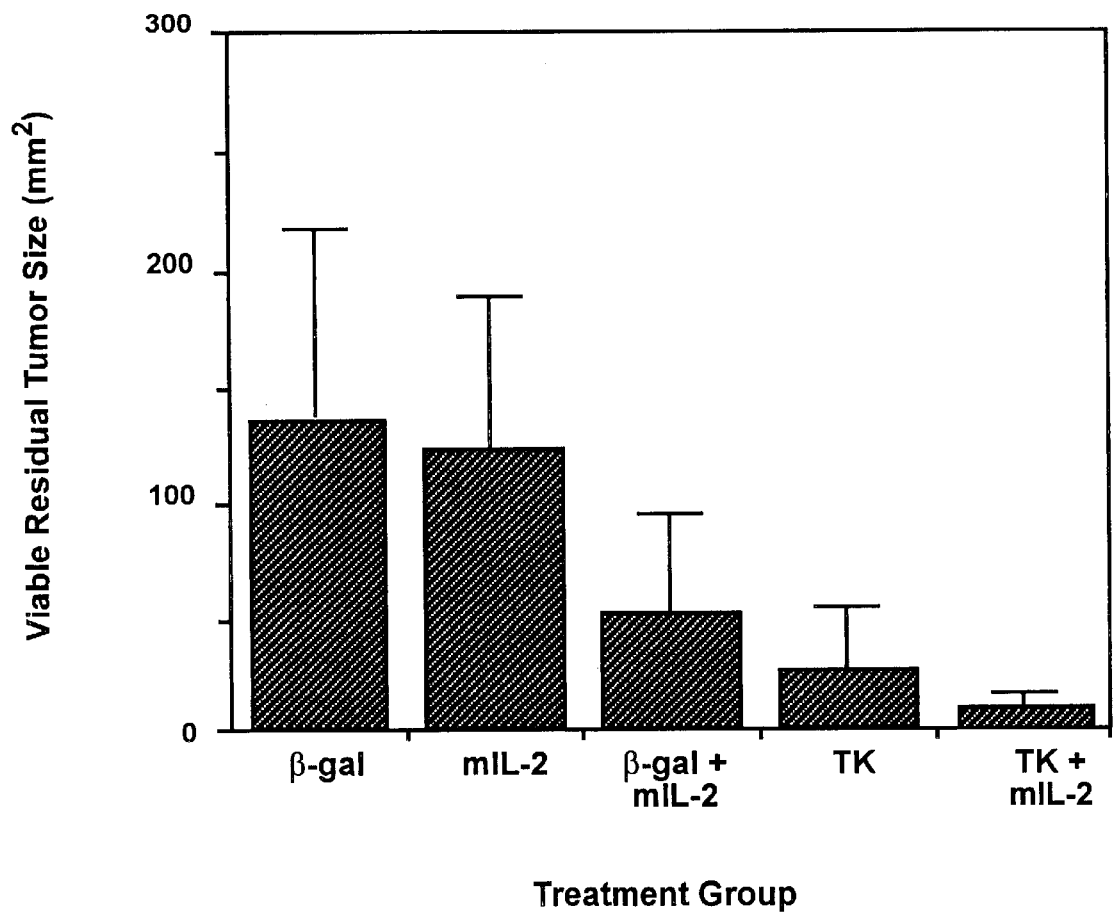
FIG. 20 demonstrates residual tumor sizes in animals after various gene therapy treatments. Maximal cross sectional areas of the tumors were measured by computerized morphometric analysis. The cumulative number of animals in the 5 treatment groups from two separate experiments were 14 (βgal); 8 (mIL2); 7 (β-gal+mIL2); 12 (tk) and 10 (tk+mIL2). The error bars represent standard deviations in each treatment group.

In order to quantify the effectiveness of tk+mIL2 combination gene therapy in causing tumor regression, computerized morphometric point count analyses of the maximal cross sectional area of the solid tumors were performed. The resulting tumor size measurements in the animals of the five treatment groups are shown in FIG. 20. All animals treated with the βgal vector developed large tumors as expected. In the animal group that was treated with the mIL2 vector alone, there was a slight but insignificant reduction in the residual tumor size. Animals treated with the βgal and mIL2 vectors together and those treated with the tk vector alone exhibited tumor necrosis and the residual tumor size was approximately 5- fold smaller than those treated with the βgal vector. In the animal group treated with both tk and mIL2 vectors, there was a significant further reduction of the residual tumor size as compared to the animal group treated with the tk vector alone.

Systemic anti-tumoral immunity in animals treated with tk+mIL2 vectors.

Figure 21:
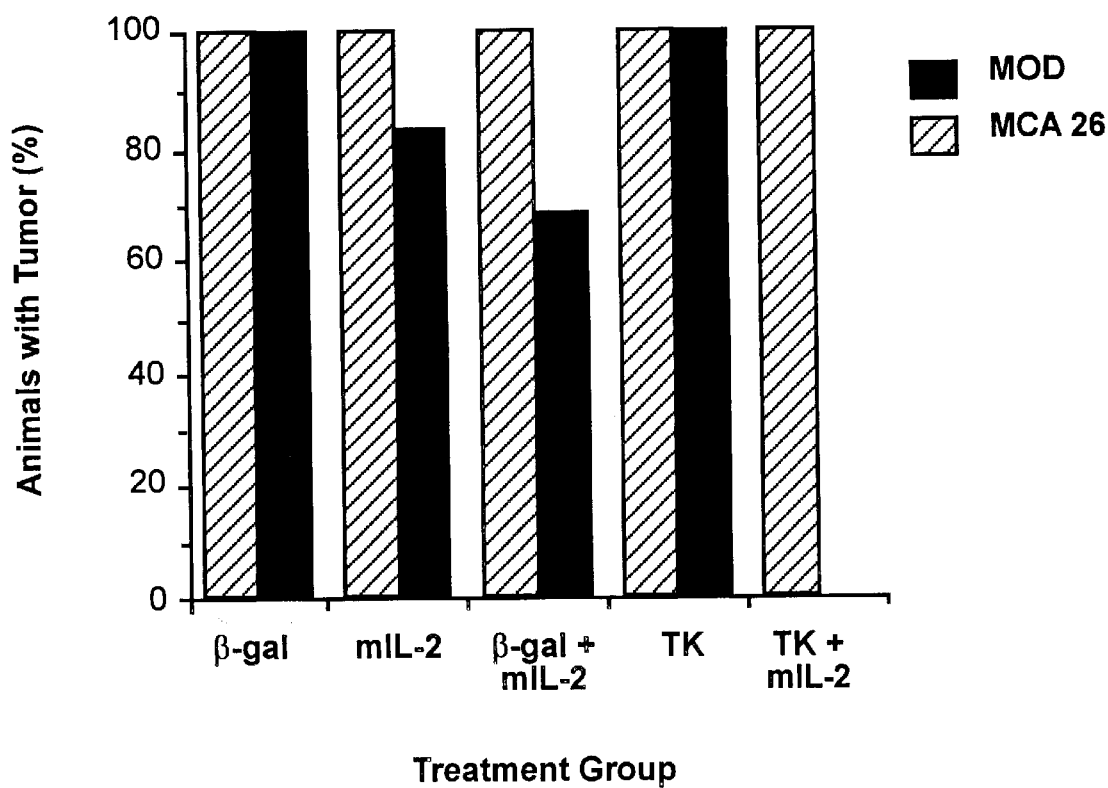
FIG. 21 shows systemic anti-tumoral immunity against parental tumor cell challenges at distal sites. Tumor cells were inoculated subcutaneously in animals of all five treatment groups. 1×10$^5$ MCA-26 cells were injected into the right flank of the animals one day after completion of GCV treatment, and 2×10$^6$ M0D breast tumor cells were injected to the left flank of the animals. These were tumorigenic doses that would result in visible tumors of similar sizes in normal BALB/c mice after 7 days. Presence of subcutaneous tumors in the challenged animals was noted visually after one week. The number of animals challenged with MCA-26 was 6 in each group and those challenged with M0D ranged between 2–4 per group.

To test whether there was any antitumoral immunity in the animals that underwent various gene therapy treatments, protection against secondary challenges by subcutaneous inoculation of tumorigenic doses of MCA- 26 cells were performed at the conclusion of GCV administration. All animals in the βgal as well as the tk vector treatment groups developed huge subcutaneous tumors at the challenge sites after 7 days. Five of 6 mIL2 vector treated and 4 of 6 β-gal+mIL2 vector treated animals also developed subcutaneous tumors at the challenge site. Of the 6 tk+mIL2 vector treated animals however, none developed subcutaneous tumors even after 4 weeks (FIG. 21). The antitumoral immunity in these animals also appeared to be MCA-26 cell specific, as no protection against distant site challenge by tumorigenic doses of a heterologous but syngeneic breast tumor cell line (MOD) was observed in the same animals (FIG. 21).

Figure 22:
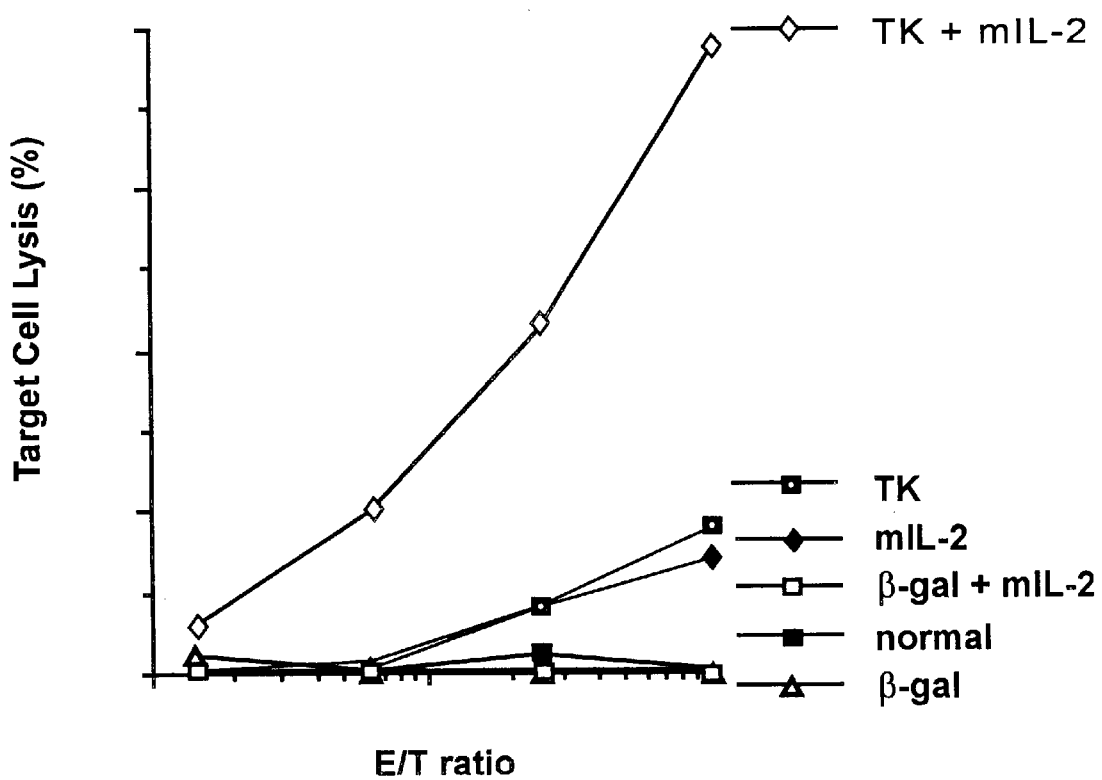
FIG. 22 shows cytotoxic T lymphocyte response in animals after various gene therapy treatments. Splenocytes were isolated from animals in various treatment groups at 3 days after the completion of GCV administration. 6×10$^6$ splenocytes were stimulated in vitro by co-cultivation with 5×10$^5$ irradiated MCA-26 cells for 5 days before the $^{51}$Cr release assays were performed. Percent MCA-26 target cell days before the $^{51}$Cr release was plotted versus various effector/target cell ratios. Data represent mean specific $^{51}$Cr release from triplicate cultures.

In order to evaluate critically whether tumor rejection was associated with sensitization of host effector cells, an in vitro cytotoxic T-lymphocyte assay was performed. Splenocytes were isolated from normal animals and from animals in all five treatment groups three days after conclusion of GCV treatment and cultured for five days with irradiated MCA-26 cells. Various numbers of the stimulated effector cell population were incubated with chromium 51-labelled target MCA-26 cells, and percent target cell lysis was plotted against the effector/target cell ratios (FIG. 22). There was no significant CTL activity against MCA-26 target cells in the splenocytes of the untreated normal mice, as well as those animals in the first four treatment groups. There was, however, a dramatic increase in MCA26 specific CTL activity in the splenocytes of animals treated with both the tk and mIL2 vectors (FIG. 22). In contrast, splenocytes of tk and mIL2 treated mice failed to lyse BALB/c derived M0D breast tumor cells or YACI target cells.

Figure 23:
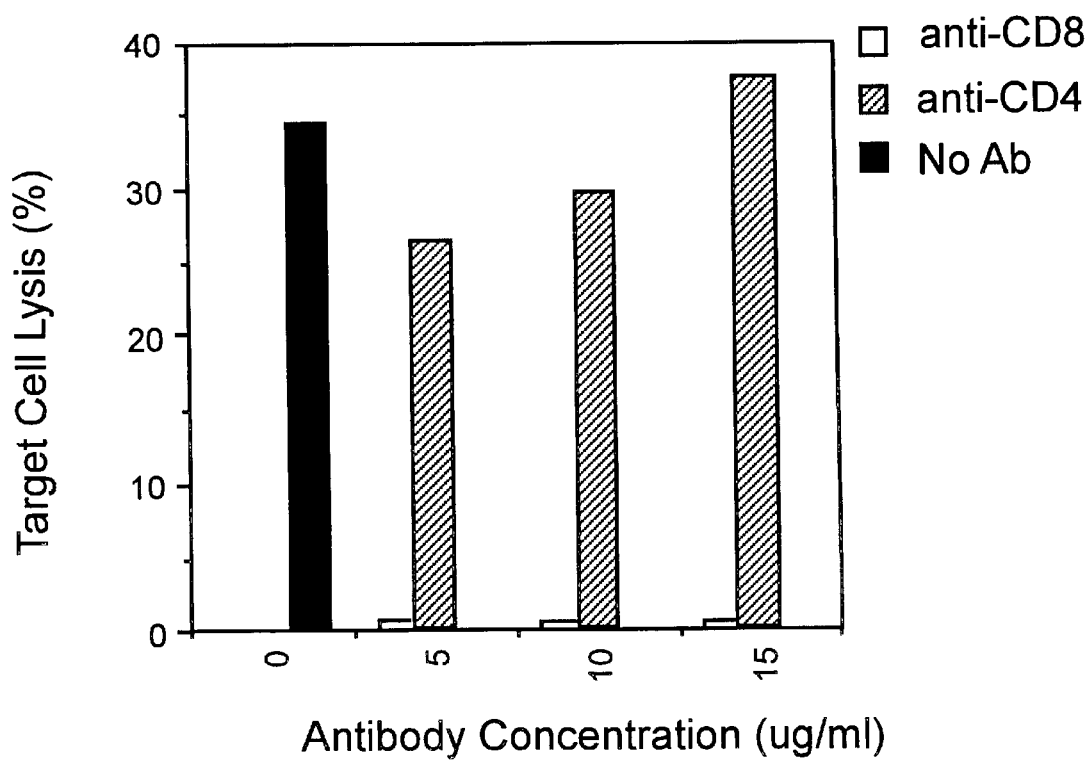
FIG. 23 shows the in vitro blocking of CTL response using monoclonal antibodies against either CD4 or CD8. Splenocytes from animals treated with ADV/RSV-tk+ADV/RSV-mIL2 were stimulated in vitro as in the legend of FIG. 5A, and the effector cells were then incubated with various concentrations of purified, sodium azide-free antibodies (GKI.5., monoclonal antibody to CD4 or 2.43, monoclonal antibody to CD8$_a$, Pharmingen) at −37° C. for 30 minutes. The $^{51}$Cr release assay was performed at an effector to target cell ratio of 50/1.

To determine whether the CTL response reflected activity of $CD4^+$ and/or $CD8^+$ T-cells, monoclonal antibodies against either CD4 or CD8 were incorporated as blocking reagents in the chromium-51 release assay. The monoclonal antibody against CD8 was effective in complete abolition of the CTL response against MCA-26 cells, while the monoclonal antibody against CD4 was ineffective (FIG. 23). These experiments provided strong evidence that CD8+ T cells from tk+mIL2 vector treated animals were responsible for MCA-26 specific cytotoxicity.

In this study, it was found that the direct delivery of the HSV-tk and mouse IL2 genes in recombinant adenoviral vectors to metastatic colon carcinoma in the liver resulted in the regression of the carcinoma in vivo. Neither the β-gal vector nor the mIL2 vector alone was capable of arresting tumor growth in this model. The tk vector alone did not cause significant necrosis, but many viable tumor cells remained. Combination therapy with both the tk and mIL2 vectors was not only more efficacious in causing tumor regression with few viable tumor cells remaining, but also resulted in the establishment of a systemic anti-tumoral immunity that effectively protected against tumorigenic doses of the parental tumor cells innocualted at distant sites. The specificity of this anti-tumoral immunity against the parental tumor cells was further illustrated by the fact that there was not anti-tumoral immunity against tumorigenic doses of a heterologous breast carcinoma cell line inoculated in the same animals. Finally, it was demonstrated that the anti-tumoral immunity in these animals was associated with the presence of MCA26 tumor specific CD8+ cytotoxic T-lymphocytes.

Interestingly, when the mIL2 vector was used in combination with $3 \times 10^9$ PFU of the β-gal vector, there was significant reduction of tumor sizes associated with the presence of inflammatory cells and tumor necrosis. This effect appeared to be associated with the total viral dose as similar results were also obtained in animals treated with the mIL2 vector+$3 \times 10^9$ PFU of the tk vector without subsequent GCV administration. The EIA recombinant adenoviral vector is known to express low levels of viral antigens that can solicit a cellular immune response against virally transduced cells in vivo, and this anti-viral immunity may be enhanced by the local expression of the interleukin-2 gene. However, there was a lack of an effective systemic CTL response to the parental tumor cells in this treatment group and 4 of 6 animals failed to exhibit protection against parental tumor cell challenge at a distant site.

EXAMPLE 6

Vector safety testing in non-human primates.

Toxicity tests of the ADV/RSV-tk and GCV treatment in baboons (Papio cvnocephalus).

Virus was produced having the titer of $1.6 \times 10^{11}$ particles/ml as determined by optical density. The vector was tested for in vitro and in vivo toxicity, tk function tests, replication competence, and contamination. Before virus injections, MRs were performed on all baboons. Pre-op samples of serum, sperm, urine, and stool were collected and tested wild-type adenovirus. Serum was tested for neutralizing antibodies to wild-type adenovirus. Three treatment groups were established.

Group 1—Moderate dose ADV/RSV-tk, with GCV, 6-week survival.

A moderate dose of ADV/RSV-tk ($1.5 \times 10^9$ particles in 10 ul PBS with 10% glycerol) was injected in the centrum semiovale of a 16.3 year old, cycling female and a 17.5 year-old male baboon. Beginning the following day, they began treatment with 10 mg/kg of GCV twice daily for 14 days. Samples were taken at 2 and 7 days post-injection for analysis for virus and anti-adenoviral antibodies. At 3 weeks following virus injection the animals were MR imaged with gadolinium enhancement. At approximately 6 weeks following virus injection, plasma, serum, urine, stool and sperm samples were again collected for analysis for the presence of shedded virus and the presence of antibodies to adenovirus, the brains were imaged with gadolinium enhancement, and the animals were necropsied.

Gross examination of the brains showed no abnormalities. Specifically, no necrotic cavities, mass effect, hemorrhage, or subarachnoid clouding were seen. The brains were sampled extensively for microscopic evidence of abnormality, and in both, small areas of macrophage infiltration and mild perivascular lymphatic cuffing were present in the centrum semiovale of the right hemisphere. No cuffing was present beyond the right hemisphere, and no white matter edema was present. No leptomeningitis was evident. No necrosis or viral inclusions were seen. The choroid plexus and ependyma were intact. No systemic pathology was seen with the exception of focal hepatic lymphocytic infiltrates without necrosis in one animal. The systemic examination in the other animal was normal.

Group 2—High dose ADV/RSV-tk, with GCV, 3-week survival.

At the FDA's explicit request two baboons were treated with a high does of ADV/RSV-tk and GCV. ADV/RSV-tk ($3\times10^{10}$ particles in 200 $\mu$l PBS with 10% glycerol) into the centrum semiovale of a 16 year-old, cycling female and a 11 year-old male baboon. The following day the animals began treatment with 10 mg/kg of GVC twice daily for 14 days via the tether system. At 2 days post-injection and at 1 week post-injection plasma, serum, urine, stool and sperm samples were collected for analysis for the presence of shedded virus and the presence of antibodies to adenovirus. It was planned that if no virus was found, the animals would be imaged with gadolinium enhancement at approximately 3 weeks following virus injection and necropsied the next day. The male baboon died 5 days after virus injection.

These animals died or were euthanized at 5 and 10 days following vector injection and initiation of GCV treatment. In both there was a 1.5 to 1.8 cm area of liquefactive necrosis at the injection site. These necrotic masses exerted mass effect. Histopathological examination revealed acute inflammation characterized by polymorphonuclear cells and lymphocytes admixed with eosinophilic liquefactive necrosis of the centrum semiovale. Radiating from the necrotic mass was cerebral edema evinced by white matter spongiosis. Intense lymphocytic perivascular cuffing was seen up to 1.5 cm away from the injection cavity in the right hemisphere. Coagulative necrosis was seen transmurally in vessels adjacent to the injection site. Rare foci of perivascular infiltrate was seen in the left hemisphere, brainstem, and cerebellum. Multifocal subarachnoid lymphocytic infiltration was present predominantly over the right hemisphere, but was present to a lesser extent over the left hemisphere and around the brainstem and cerebellum. No choroid plexus or ependymal destruction was present although focal choroid plexus inflammation was seen on the right in the animal surviving for 10 days. No viral intranuclear inclusions were seen. Luxol fast blue stained sections disclosed no loss of myelin except in the necrotic cavities.

Systemic examination disclosed congested lungs in the animal dying on day 5; and microscopic examination demonstrated eosinophilic material filling the alveolar spaces suggestive of neurogenic pulmonary edema. No pulmonary inflammation was present. The animal euthanized at 10 days showed no systemic pathology.

Group 3—High dose ADV/RSV-tk, no GCV treatment, 3- and 5-week survival.

To differentiate between the effect of virus injection and virus injection plus GCV administration 2 male baboons (10.5 and 11.5 year-old) were injected with $3\times10^{10}$ particles of ADV/RSV-tk in the same manner as above. These two animals were not treated with GCV. Samples were taken and analyzed as described above. One baboon was necropsied at 3 weeks after the first post-injection MR. The other baboon was necropsied at 6 weeks after the second MR. Tissue and fluid samples were analyzed as above.

The animal examined at three weeks had a 1.5 cm cystic cavity in the right centrum semiovale. No mass effect, herniation, or hemorrhage was grossly present. Histopathologically, the cavity was filled with macrophages containing lipid debris. Adjacent to the cavity was mild gliosis, persistent lymphocytic inflammation, perivascular lymphocytic cuffing, and minimal white matter edema. No viral inclusions were seen, and the choroid plexus and ependyma were intact. Mild focal subarachnoid space collections of lymphocytes were present over the right hemisphere, but not the left or around the brainstem. No systemic pathological alterations were present.

The animal examined at six weeks after treatment had a 1.6 cm slightly irregular cystic cavity in the right posterior centrum semiovale. The lining of the cavity wall was light brown, and no mass effect, herniation, or hematoma was evident. Microscopic examination demonstrated lipid-laden macrophages within the cavity wall, persistent lymphocytic infiltrate in the wall and around nearby blood vessels, and minimal edema and gliosis immediately adjacent to the cavity. No choroid plexus, ependymal, and or residual leptomeningeal infiltrate was seen. No systemic pathological alterations were present.

In summary, there appears to be a dose dependent neurotoxic effect of vector with high dose treatment groups having coagulative necrosis at the injection site which over time is cleared by macrophages to produce cystic cavities. The process persists for six weeks although the inflammatory component is resolving by this point. GCV appears to potentiate the clinical toxicity of the high dose vector since both animals receiving high does vector plus GCV died or became ill enough to require euthanasia. The moderate dose vector plus GCV animals exhibited only microscopic evidence of neurotoxicity at the injection site. The adenoviral vector exerts dose dependent cytopathic effects via the penton structural proteins paralleling the cytopathic effect of wild type adenovirus. In this experiment, the fact that the high dose groups both with and without GC had necrosis while the moderate does animals receiving GVC did not, strongly suggests direct cytopathic effect of vector rather than toxicity arising from 6k conversion of BVC to toxic compounds. This experiment establishes the dosage threshold for cytopathology of $1.5\times10^9$ particles. Vector dosage below this threshold coupled with BVC is toxic to dividing tumor cells while sparing non-dividing CNS cellular constituents.

MRI Analysis of Baboon Brains Treated with Moderate and High Doses of ADV/RSV-tk.

The gross neuropathological alterations appear to be reflected in the MRI findings. Unfortunately, our high dose vector plus GCV animals succumbed before follow-up MRI's could be obtained. The high dose vector without GCV animals both exhibited areas of high signal intensity on T2 weighted images at three weeks corresponding to the cystic cavities seen at three and six weeks at necropsy. At three weeks some minimal mass effect was demonstrable by MRI. The six week MRI of the remaining animal in this group showed better delineation of the cystic cavity corresponding to the gross pathological finding of a resolving circumscribed cavity. Leakage of gadolinium was seen in these animals corresponding to the inflammatory changes around blood vessels. The moderate dose vector plus GCV animals exhibited much less impressive MRI alterations, and no cavity formation was seen by imaging or gross inspection corresponding to the lower toxic effect of the treatment regimen. These results indicate that MRI can be used to monitor tissue effects of this therapy.

PCR Analysis of Tissues from Baboons Injected with Moderate and High Doses of ADV/RSV-tk.

Necropsy tissue (2–3 mm diameter) was used for the analysis. In cases of larger organ specimens (brain, liver, etc.) multiple (4 to 6) tissue samples were collected and pooled. Total DNA was isolated using SDS and proteinase K (Ausubel et al., 1987). A 1 µl aliquot of DNA from each sample was used in the PCR reaction. The primer oligonucleotides used were a sense primer Adv.3205 (5'-GTGTTACTCATAGCGTAA-3') and an antisense primer RSV 270A (5'-GACTCCTAACCGCGACA-3'), the former primer situated in the adenoviral and the latter in the RSV-LTR sequences and both 5' of the thymidine kinase gene in the recombinant plasmid pADL-1/RSV-tk used to generate the recombinant virus. The PCR reaction was carried out for 30 cycles of 30s @ 92° C., 30 s @ 50° C., and 1 m @ 72° C. The reaction mixture consisted of 50 µM of each dNTP nd 50 pM of each of the primers and 4 units of Taq polymerase in a total volume of 100 µl (Saiki, 1990). At the end of PCR a 10 µl aliquot of the product was electrophoresed on a 4% NuSieve Agarose gel. The gel was stained with ethydium bromide and visualized under UV light. Those samples that yielded a 232 bp fragment as seen on the gel were scored positive. The site of injection was positive in 3 of the 4 animals that received high doses of virus. One animal that had virus sequence at the injection site also had virus in its spinal cord. The other two animals that were positive at the injection site were negative in other areas of the CNS. No other tissues, including gonadal tissue, were positive for ADV/RSV-tk sequences. The results of the analysis are listed in Table III.

TABLE III

PCR analysis of tissues from baboons injected with AVD/RSV-tk. ND = not done.

| ORGAN | Mod. dose + GCV; ♀ | Mod. dose + GCV; ♂ | High dose + GCV; ♀ | High dose + GCV; ♂ | High dose – GCV; ♂ | High dose – GCV; ♂ |
|---|---|---|---|---|---|---|
| Injection site | – | – | + | + | + | – |
| CNS distal to site | – | – | + | – | – | – |
| Lung | ND | – | ND | – | – | – |
| Kidney | – | – | – | – | – | ND |
| Ovary/Testis | * | – | – | – | – | – |

All patents and publications mentioned in this specification are indicative of the levels of those skilled in the art to which the invention pertains. All patents and publications are herein incorporated by reference to the same extent as if each individual publication is specifically and individually indicated to be incorporated by reference.

One skilled in the art will readily appreciate that the present invention is well adapted to carry out the objects and obtain the ends and advantages mentioned, as well as those inherent therein. The methods, procedures, treatments, molecules, and specific compounds described herein are presently representative of preferred embodiments, are exemplary and are not intended as limitations on the scope of the invention. Changes therein and other uses will occur to those skilled in the art which are encompassed within the spirit of the invention and are defined by the scope within the claims.

We claim:

1. A method of causing regression of a solid tumor in a mammal, comprising the steps of:

administering an adenoviral vector directly into said tumor, wherein said vector is comprised of a DNA sequence encoding a suicide gene, and one or more cytokine genes, wherein said genes are operably linked to a promoter, and wherein said tumor expresses said suicide gene and said one or more cytokine genes; and administering a prodrug in amounts sufficient to cause regression of said tumor when said prodrug is converted to a toxic compound by said suicide gene.

2. The method of claim 1, wherein the suicide gene sequence expressed codes for a protein selected from the group consisting of thymidine kinase of herpes simplex virus, thymidine kinase of varicella zoster virus and bacterial cytosine deaminase.

3. The method of claim 1, wherein said one or more cytokine gene sequences is selected from the group consisting of interleukin-1, interleukin-2, interleukin-4, interleukin-6, interleukin-7, interleukin-10, interleukin-12, interferon-α, interferon-β, interferon-δ, tumor necrosis factor-α, tumor necrosis factor-β, granulocyte-macrophage colony stimulating factor (GM-CSF) and granulocyte colony stimulating factor (G-CSF).

4. The method of claim 1, wherein solid tumor is selected from the group consisting of colon, prostate, breast, lung, skin, liver, bone, pancreas, ovary, testis, bladder, kidney, brain, head and neck cancer.

5. The method of claim 1, wherein said solid tumor is selected from the group consisting of squamous cell papilloma, choroid plexus papilloma and laryngeal papilloma.

6. The method of claim 1, wherein said solid tumor is selected from the group consisting of genital warts, plantar warts, epidermodysplasia verruciformis and malignant warts.

7. The method of claim 1, wherein the suicide gene sequence to be expressed is thymidine kinase of herpes simplex virus and the prodrug is ganciclovir, acyclovir, FIAU or their derivatives.

8. The method of claim 1, wherein the suicide gene sequence to be expressed is bacteria cytosine deaminase and the prodrug is 5-fluorocytosine or its derivatives.

9. The method of claim 1, wherein the suicide gene sequence to be expressed is varicella zoster virus thymidine kinase and the prodrug is 6-methoxypurine arabinoside or its derivatives.

10. The method of claim 1, wherein said prodrug is selected from the group consisting of ganciclovir, acyclovir, 1-5-iodouracil FIAU, 5-fluorocytosine, 6-methoxypurine arabinoside and their derivatives.

11. The method of claim 10, wherein said ganciclovir is administered in a dose of about 1 mg/day/kg to about 20 mg/day/kg body weight.

12. The method of claim 10, wherein said acyclovir is administered in a dose of from about 1 mg/day/kg to about 100 mg/day/kg body weight.

13. The method of claim 10, wherein s aid FIAU is administered in a dose of from about 1 mg/day/kg to about 50 mg/day/kg body weight.

14. A method of causing regression of a solid tumor in a mammal, comprising the steps of:

introducing a first adenoviral vector and a second adenoviral vector directly into said solid tumor; said first adenoviral vector comprised of a DNA sequence encoding a suicide gene operatively linked to a promoter and wherein said tumor expresses the suicide gene; and said second adenoviral vector comprised of a DNA sequence encoding a cytokine gene operatively linked to a promoter and wherein said tumor expresses the cytokine gene; and administering a prodrug in amounts sufficient to cause regression of said tumor when said prodrug is converted to a toxic compound by said suicide gene.

15. The method of claim 14, wherein said promoters are selected from the group consisting of Rous Sarcoma Virus—Long Terminal Repeat, cytomegalovirus promoter, murine leukemia virus—long terminal repeat, simian virus 40 early and late promoters, and herpes simplex virus-thymidine kinase promoter.

16. The method of claim 14, wherein the suicide gene sequence expressed codes for a protein selected from the group consisting of thymidine kinase of herpes simplex virus, thymidine kinase of varicella zoster virus and bacterial cytosine deaminase.

17. The method of claim 14, wherein the additional adenoviral vectors contain one or more cytokine gene sequence coding for proteins selected from the group consisting of interleukin-1, interleukin-2, interleukin-4, interleukin-6, interleukin-7, interleukin-10, interleukin-12, interferon-$\alpha$, interferon-$\beta$, interferon-$\delta$, tumor necrosis factor-$\alpha$, tumor necrosis factor-$\beta$, granulocyte-macrophage colony stimulating factor (GM-CSF) and granulocyte colony stimulating factor (G-CSF).

18. The method of claim 14, wherein solid tumor is selected from the group consisting of colon, prostate, breast, lung, skin, liver, bone, pancreas, ovary, testis, bladder, kidney, brain, head and neck cancer.

19. The method of claim 14, wherein said solid tumor is selected from the group consisting of squamous cell papilloma, choroid plexus papilloma and laryngeal papilloma.

20. The method of claim 14, wherein said solid tumor is selected from the group consisting of genital warts, plantar warts, epidermodysplasia verruciformis and malignant warts.

21. The method of claim 14, wherein the suicide gene sequence to be expressed is thymidine kinase of herpes simplex virus and the prodrug is ganciclovir, acyclovir, FIAU or their derivatives.

22. The method of claim 14, wherein the suicide gene sequence to be expressed is bacterial cytosine deaminase and the prodrug is 5-fluorocytosine or its derivatives.

23. The method of claim 14, wherein the suicide gene sequence to be expressed is varicella zoster virus thymidine kinase and the prodrug is 6-methoxypurine arabinoside or its derivatives.

24. The method of claim 14, wherein said tumor is liver cancer and said promoter is selected from the group consisting of an albumin promoter, an alpha-fetoprotein promoter, an $\alpha$-antitrypsin promoter and a phosphoenol pyruvate carboxykinase promoter.

25. The method of claim 14, wherein said tumor is colon cancer and said promoter is a carbonic anhydrase I promoter or a carcinoembryogenic antigen promoter.

26. The method of claim 14, wherein said tumor is ovarian cancer and said promoter is selected from the group consisting of an estrogen promoter, an aromatase cytochrome P450 promoter, a cholesterol side chain cleavage P450 and a 17 alpha-hydroxylase P450 promoter.

27. The method of claim 14, wherein said tumor is prostate cancer and said promoter is selected from the group consisting of a prostate specific antigen promoter, a gp91-phox gene promoter and a prostate-specific kallikrein promoter.

28. The method of claim 14, wherein said tumor is breast cancer and the promoter is selected from the group consisting of an erb-$B_2$ promoter, an erb-$B_3$ promoter, $\beta$-casein promoter, WAB (whey acidic protein) promoter and $\beta$-lactoglobulin promoter.

29. The method of claim 14, wherein said tumor is lung cancer and the promoter is selected from the group consisting of a surfactant promoter, a carcinoembryonic antigen promoter and Uroglobin promoter.

30. The method of claim 14, wherein said tumor is skin cancer and the promoter is selected from the group consisting of a human keratin 1 promoter, human keratin 6 promoter and loicrin promoter.

31. The method of claim 14, wherein said tumor is brain cancer and the promoter is selected from the group consisting of a glial fibrillary acidic protein promoter, a mature astrocyte specific protein myelin promoter and a tyrosine hydroxylase promoter.

32. The method of claim 14, wherein said tumor is pancreatic cancer and the promoter is selected from the group consisting of a villin promoter, a glucagon promoter, an islet amyloid polypeptide (amylin) promoter and insulin promoter.

33. The method of claim 14, wherein said tumor is thyroid cancer and the promoter is selected from the group consisting of a thyroglobulin promoter and a calcitonin promoter.

34. The method of claim 14, wherein said tumor is bone cancer and the promoter is selected from the group consisting of an Alpha 1 (I) collagen promoter, osteocalcin promoter and sialoglycoprotein promoter.

35. The method of claim 14, wherein said tumor is kidney cancer and the promoter is selected from the group consisting of a renin promoter, a liver/bone/kidney alkaline phosphatase promoter and erythropoietin (epo) promoter.

36. The method of claim 14, wherein said prodrug is selected from the group consisting of ganciclovir, acyclovir, 1-5-iodouracil FIAU, 5-fluorocytosine, 6-methoxypurine arabinoside and their derivatives.

37. The method of claim 36, wherein said ganciclovir is administered in a dose of about 1 mg/day/kg to about 20 mg/day/kg body weight.

38. The method of claim 36, wherein said acyclovir is administered in a dose of from about 1 mg/day/kg to about 100 mg/day/kg body weight.

39. The method of claim 36, wherein said FIAU is administered in a dose of from about 1 mg/day/kg to about 50 mg/day/kg body weight.

40. A method of causing regression of a solid tumor in a mammal, comprising the steps of:

administering an adenoviral vector directly into said tumor, wherein said vector or vectors are comprised of a DNA sequence encoding a suicide gene selected from the group consisting of genes encoding HSV-tk or VZV-tk, and a gene encoding IL-2, wherein said genes are operably linked to a promoter, and wherein said tumor expresses said suicide gene and said IL-2 gene; and administering a prodrug in amounts sufficient to cause regression of said tumor when said prodrug is converted to a toxic compound by said suicide gene.

41. The method of claim 40 wherein said suicide gene encodes HSV-tk.

42. The method of claim 40 wherein said suicide gene encodes VZV-tk.

43. A method of causing regression of a solid tumor in a mammal, comprising the steps of:

introducing a first adenoviral vector and a second adenoviral vector directly into said solid tumor;

said first adenoviral vector comprised of a DNA sequence encoding a suicide gene, selected from the group consisting of genes encoding HSV-tk and VZV-tk, operatively linked to a promoter and wherein said tumor expresses the suicide gene;

and said second adenoviral vector comprised of a DNA sequence encoding a cytokine gene encoding IL-2 operatively linked to a promoter and wherein said tumor expresses the cytokine gene; and administering a prodrug in amounts sufficient to cause regression of said tumor when said prodrug is converted to a toxic compound by said suicide gene.

44. The method of claim 43 wherein said suicide gene encodes HSV-tk.

45. The method of claim 43 wherein said suicide gene encodes VZV-tk.

* * * * *